United States Patent
Xu et al.

(10) Patent No.: US 12,006,542 B2
(45) Date of Patent: Jun. 11, 2024

(54) FORCE-MODULATED HYBRIDIZATION FOR VISUALIZING NUCLEIC ACID LENGTH AND FUNCTION

(71) Applicant: University of Houston System, Houston, TX (US)

(72) Inventors: Shoujun Xu, Houston, TX (US); Qiongzheng Hu, Houston, TX (US); Yuhong Wang, Houston, TX (US)

(73) Assignee: University of Houston System, Houston, TX (US)

( * ) Notice: Subject to any disclaimer, the term of this patent is extended or adjusted under 35 U.S.C. 154(b) by 1144 days.

(21) Appl. No.: 16/620,571

(22) PCT Filed: Jun. 11, 2018

(86) PCT No.: PCT/US2018/036885
§ 371 (c)(1),
(2) Date: Dec. 9, 2019

(87) PCT Pub. No.: WO2018/227182
PCT Pub. Date: Dec. 13, 2018

(65) Prior Publication Data
US 2023/0160003 A1    May 25, 2023

Related U.S. Application Data

(60) Provisional application No. 62/517,694, filed on Jun. 9, 2017.

(51) Int. Cl.
*C12Q 1/6811* (2018.01)
*B01L 3/00* (2006.01)
(Continued)

(52) U.S. Cl.
CPC ...... *C12Q 1/6874* (2013.01); *B01L 3/502761* (2013.01); *B01L 7/52* (2013.01);
(Continued)

(58) Field of Classification Search
None
See application file for complete search history.

(56) References Cited

U.S. PATENT DOCUMENTS 4,312,593 A     1/1982   Baker et al.
6,159,686 A  *  12/2000  Kardos ............. G01N 21/6428
                                                          435/7.1
(Continued)

OTHER PUBLICATIONS

Pettersson, E., et al., "A novel method for rapid hybridization of DNA to a solid support", PLoS One, 2013, vol. 8, No. 8, pp. 1-5 See abstract; and pp. 2-3.
(Continued)

*Primary Examiner* — Robert T. Crow
(74) *Attorney, Agent, or Firm* — Shackelford, McKinley & Norton, LLP

(57) ABSTRACT

Embodiments of the present disclosure pertain to methods of utilizing force-modulated hybridization to determine the length of an analyte strand, to determine an unknown nucleic acid sequence, or to determine the binding of a nucleotide to an active agent. Additional embodiments of the present disclosure pertain to sample holder devices and methods of utilizing such devices. Further embodiments of the present disclosure pertain to detection devices.

11 Claims, 17 Drawing Sheets

Specification includes a Sequence Listing.

(51) Int. Cl.
  B01L 7/00 (2006.01)
  C12Q 1/6816 (2018.01)
  C12Q 1/6874 (2018.01)
  C12Q 1/6806 (2018.01)
  C12Q 1/6818 (2018.01)

(52) U.S. Cl.
  CPC . *B01L 2200/0663* (2013.01); *B01L 2300/044* (2013.01); *B01L 2300/0654* (2013.01); *B01L 2300/0672* (2013.01); *B01L 2300/18* (2013.01); *B01L 2400/0439* (2013.01); *C12Q 1/6806* (2013.01); *C12Q 1/6818* (2013.01)

(56) References Cited

U.S. PATENT DOCUMENTS

| | | | |
|---|---|---|---|
| 6,549,276 | B1 | 4/2003 | Longtin |
| 2003/0064393 | A1 | 4/2003 | Bass et al. |
| 2004/0009514 | A1 | 1/2004 | Frutos et al. |
| 2004/0086867 | A1 | 5/2004 | Han |
| 2007/0212710 | A1* | 9/2007 | Mittmann ............ C12Q 1/6816 536/24.3 |
| 2011/0250599 | A1* | 10/2011 | Becker ................ C12Q 1/6837 436/501 |
| 2014/0309134 | A1 | 10/2014 | Xu et al. |

OTHER PUBLICATIONS

De Silva, L., et al., "Well-Defined and Sequence-Specific Noncovalent Binding Forces of DNA", J. Phys. Chem. B 2013, 117, 7554-7558.

Hu, Q., et al., "Sequence and Chiral Selectivity of Drug-DNA Interactions Revealed by Force Spectroscopy", Angew. Chem. Int. Ed. 2014, 53, 14135-14138.

Jia, H. et al., "Probing drug-DNA interactions using superresolution force spectroscopy", Appl. Phys. Lett. 113, 193702 (2018); https://doi.org/10.1063/1.5045787.

Jia, H. et al., "Super-resolution force spectroscopy reveals ribosomal motion at sub-nucleotide steps", Chem. Commun., 2018, 54, 5883-5886.

\* cited by examiner

FIG. 2A
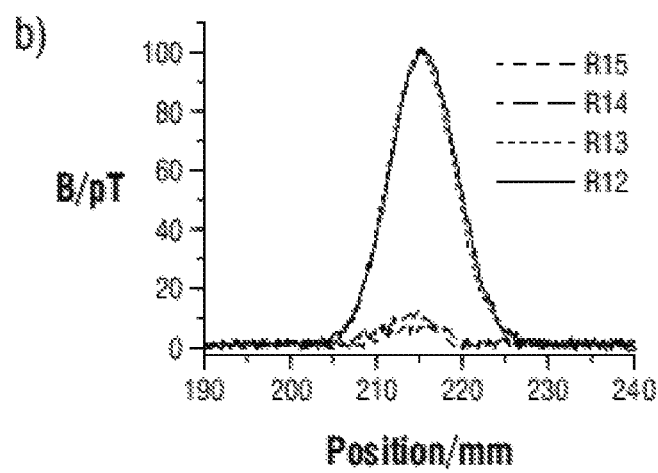
FIG. 2B
FIG. 2C
FIG. 2

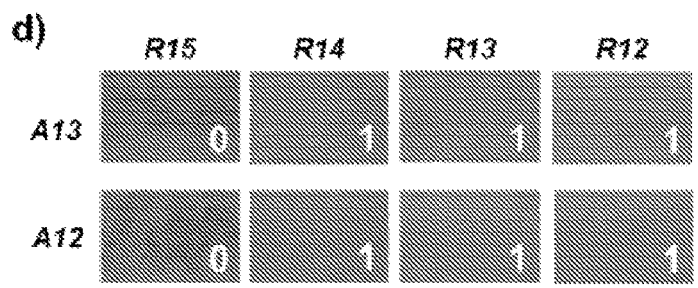
FIG. 2D
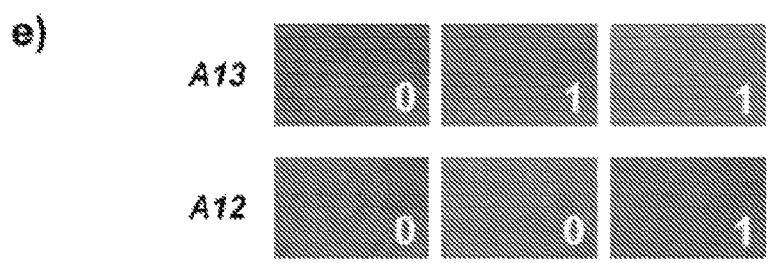
FIG. 2E
FIG. 2

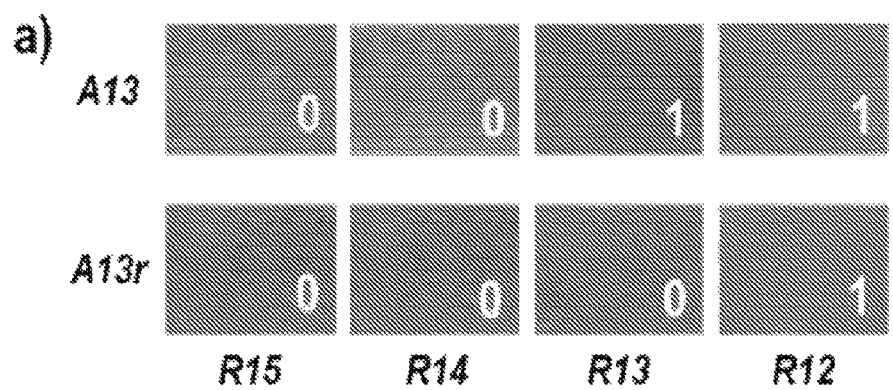
FIG. 3A
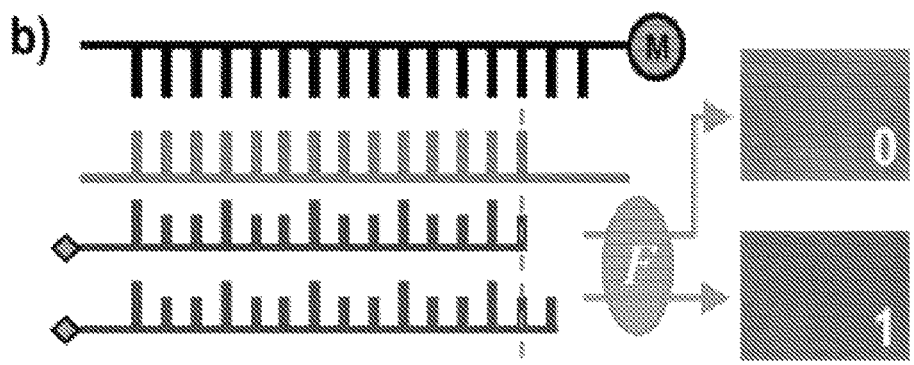
FIG. 3B
FIG. 3 a)
(SEQ ID NO: 19)
(SEQ ID NO: 20)
FIG. 4A
b)
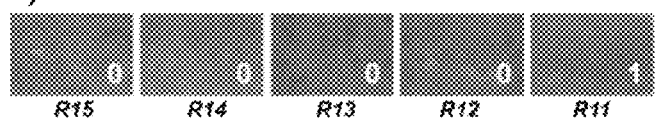
FIG. 4B
c)
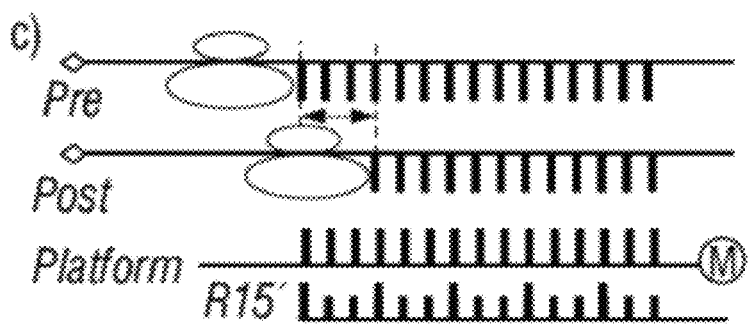
FIG. 4C
FIG. 4D
FIG. 4

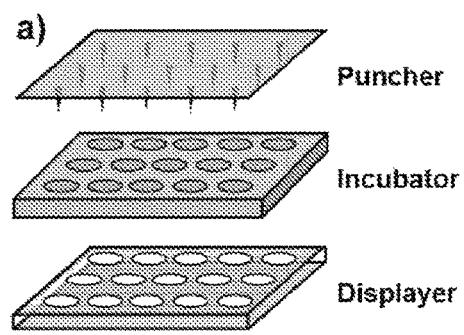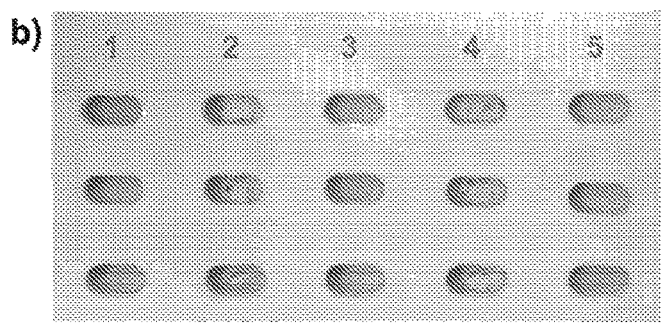
FIG. 7A  FIG. 7B
FIG. 7

```
                        SEQUENCE LISTING

<160> NUMBER OF SEQ ID NOS: 22

<210> SEQ ID NO 1
<211> LENGTH: 13
<212> TYPE: DNA
<213> ORGANISM: Artificial Sequence
<220> FEATURE:
<223> OTHER INFORMATION: A13

<400> SEQUENCE: 1
cagactgact cga                                                        13

<210> SEQ ID NO 2
<211> LENGTH: 12
<212> TYPE: DNA
<213> ORGANISM: Artificial Sequence
<220> FEATURE:
<223> OTHER INFORMATION: A12

<400> SEQUENCE: 2
cagactgact cg                                                         12

<210> SEQ ID NO 3
<211> LENGTH: 13
<212> TYPE: DNA
<213> ORGANISM: Artificial Sequence
<220> FEATURE:
<223> OTHER INFORMATION: A13r

<400> SEQUENCE: 3
cagactgact cga                                                        13

<210> SEQ ID NO 4
<211> LENGTH: 15
<212> TYPE: DNA
<213> ORGANISM: Artificial Sequence
<220> FEATURE:
<223> OTHER INFORMATION: Magnetically labeled oligonucleotide strand

<400> SEQUENCE: 4
gatcgagtca gtctg                                                      15

<210> SEQ ID NO 5
<211> LENGTH: 15
<212> TYPE: DNA
<213> ORGANISM: Artificial Sequence
<220> FEATURE:
<223> OTHER INFORMATION: R15

<400> SEQUENCE: 5
cagactgact cgatc                                                      15
```

```
<210> SEQ ID NO 6
<211> LENGTH: 14
<212> TYPE: DNA
<213> ORGANISM: Artificial Sequence
<220> FEATURE:
<223> OTHER INFORMATION: R14

<400> SEQUENCE: 6
cagactgact cgat                                                        14

<210> SEQ ID NO 7
<211> LENGTH: 13
<212> TYPE: DNA
<213> ORGANISM: Artificial Sequence
<220> FEATURE:
<223> OTHER INFORMATION: R13

<400> SEQUENCE: 7
cagactgact cga                                                         13

<210> SEQ ID NO 8
<211> LENGTH: 12
<212> TYPE: DNA
<213> ORGANISM: Artificial Sequence
<220> FEATURE:
<223> OTHER INFORMATION: R12

<400> SEQUENCE: 8
cagactgact cg                                                          12

<210> SEQ ID NO 9
<211> LENGTH: 11
<212> TYPE: DNA
<213> ORGANISM: Artificial Sequence
<220> FEATURE:
<223> OTHER INFORMATION: R11

<400> SEQUENCE: 9
cagactgact c                                                           11

<210> SEQ ID NO 10
<211> LENGTH: 75
<212> TYPE: RNA
<213> ORGANISM: Artificial Sequence
<220> FEATURE:
<223> OTHER INFORMATION: mRNA (Pre)

<400> SEQUENCE: 10
caacuguuaa uuaaauuaaa uuaaaaagga aauaaaaaug uuugaaagua aguacguaaa      60
ucuacugcug aacuc                                                       75

<210> SEQ ID NO 11
<211> LENGTH: 75
<212> TYPE: RNA
<213> ORGANISM: Artificial Sequence
<220> FEATURE:
<223> OTHER INFORMATION: mRNA (Post)

<400> SEQUENCE: 11
caacuguuaa uuaaauuaaa uuaaaaagga aauaaaaaug uuugaaagua aguacguaaa      60
ucuacugcug aacuc                                                       75

<210> SEQ ID NO 12
```

-continued

<211> LENGTH: 21
<212> TYPE: DNA
<213> ORGANISM: Artificial Sequence
<220> FEATURE:
<223> OTHER INFORMATION: R15'

<400> SEQUENCE: 12
ctcaagagca gtagatttac g                                                  21

<210> SEQ ID NO 13
<211> LENGTH: 15
<212> TYPE: DNA
<213> ORGANISM: Artificial Sequence
<220> FEATURE:
<223> OTHER INFORMATION: Magnetically labeled oligonucleotide strand

<400> SEQUENCE: 13
gtctgactga gctag                                                         15

<210> SEQ ID NO 14
<211> LENGTH: 12
<212> TYPE: DNA
<213> ORGANISM: Artificial Sequence
<220> FEATURE:
<223> OTHER INFORMATION: Analyte strand

<400> SEQUENCE: 14
cagactgact cg                                                            12

<210> SEQ ID NO 15
<211> LENGTH: 13
<212> TYPE: DNA
<213> ORGANISM: Artificial Sequence
<220> FEATURE:
<223> OTHER INFORMATION: Oligonucleotide ruler strand

<400> SEQUENCE: 15
cagactgact cga                                                           13

<210> SEQ ID NO 16
<211> LENGTH: 13
<212> TYPE: DNA
<213> ORGANISM: Artificial Sequence
<220> FEATURE:
<223> OTHER INFORMATION: Oligonucleotide ruler strand

<400> SEQUENCE: 16
cagactgact cgt                                                           13

<210> SEQ ID NO 17
<211> LENGTH: 13
<212> TYPE: DNA
<213> ORGANISM: Artificial Sequence
<220> FEATURE:
<223> OTHER INFORMATION: Oligonucleotide ruler strand

<400> SEQUENCE: 17
cagactgact cgg                                                           13

<210> SEQ ID NO 18
<211> LENGTH: 13
<212> TYPE: DNA
<213> ORGANISM: Artificial Sequence
<220> FEATURE:
<223> OTHER INFORMATION: Oligonucleotide ruler strand

<400> SEQUENCE: 18
cagactgact cgc                                                                  13

<210> SEQ ID NO 19
<211> LENGTH: 22
<212> TYPE: DNA
<213> ORGANISM: Artificial Sequence
<220> FEATURE:
<223> OTHER INFORMATION: Sequence for determining binding site of
      endonuclease DpnII

<400> SEQUENCE: 19
cagactgact cgatcacttg tc                                                        22

<210> SEQ ID NO 20
<211> LENGTH: 22
<212> TYPE: DNA
<213> ORGANISM: Artificial Sequence
<220> FEATURE:
<223> OTHER INFORMATION: Sequence for determining binding site of
      endonuclease DpnII

<400> SEQUENCE: 20
gtctgactga gctagtgaac ag                                                        22

<210> SEQ ID NO 21
<211> LENGTH: 29
<212> TYPE: DNA
<213> ORGANISM: Artificial Sequence
<220> FEATURE:
<223> OTHER INFORMATION: DNA duplex having two enzyme-binding segments
      for DpnII and EcoRI

<400> SEQUENCE: 21
ctgttcacta gctcagtctt aagactgac                                                 29

<210> SEQ ID NO 22
<211> LENGTH: 35
<212> TYPE: DNA
<213> ORGANISM: Artificial Sequence
<220> FEATURE:
<223> OTHER INFORMATION: DNA duplex having two enzyme-binding segments
      for DpnII and EcoRI

<400> SEQUENCE: 22
gacaagtgat cgagtcagaa ttctgactgt aataa                                          35

FORCE-MODULATED HYBRIDIZATION FOR VISUALIZING NUCLEIC ACID LENGTH AND FUNCTION

CROSS-REFERENCE TO RELATED APPLICATIONS

This application claims priority to U.S. Provisional Patent Application No. 62/517,694, filed on Jun. 9, 2017. The entirety of the aforementioned application is incorporated herein by reference.

STATEMENT REGARDING FEDERALLY SPONSORED RESEARCH

This invention was made with government support under GM111452 awarded by the National Institutes of Health, and 1508845 awarded by the National Science Foundation. The government has certain rights in the invention.

FIELD OF THE INVENTION

The present disclosure relates to methods and devices for determining a nucleic acid's length and function.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Nucleic acids, which carry genetic information for all life forms, are ubiquitously involved in biological functions. Measuring their exact interacting sites with other biological entities is therefore fundamental to investigating their roles in various functions. Examples include the binding sites of enzymes and inhibitors, and the dynamic positions of mRNA relative to the ribosome. Thus, there remains a need in the art for new instrumentation and methods for precisely measuring nucleic acids, and ideally achieve single nucleotide (nt) resolution.

SUMMARY OF THE DISCLOSURE

In some embodiments, the present disclosure pertains to methods of determining the length of an analyte strand by (a) incubating a magnetically labeled oligonucleotide strand, the analyte strand, and one of a series of oligonucleotide ruler strands to form a mixture, where the magnetically labeled oligonucleotide strand is complementary in sequence to the analyte strand, where the series of oligonucleotide ruler strands are complementary in sequence to the magnetically labeled oligonucleotide strand and include different lengths, and where either the analyte strand or the oligonucleotide ruler strands are labeled with at least one label; (b) transferring the mixture to a surface functionalized to couple with the at least one label; (c) applying a mechanical force to the mixture; and (d) inspecting the surface for immobilized particles.

If the analyte strand is labeled, then the longest oligonucleotide ruler strand producing immobilized particles on the surface represents the length of the analyte strand. However, if the oligonucleotide ruler strands are labeled, then the longest oligonucleotide ruler strand not producing immobilized particles represents the length of the analyte strand. In some embodiments, a different oligonucleotide ruler strand is used to repeat steps (a)-(d) until the length of the analyte strand is determined.

In some embodiments, the present disclosure pertains to methods of determining an unknown nucleic acid sequence of a magnetically labeled oligonucleotide strand by (a) incubating the magnetically labeled oligonucleotide strand, an analyte strand, and one of a series of oligonucleotide ruler strands to form a mixture, where the analyte strand is complementary in sequence to at least some of the known sequences of the magnetically labeled oligonucleotide strand, where the series of oligonucleotide ruler strands are complementary in sequence to the magnetically labeled oligonucleotide strand, and where the oligonucleotide ruler strands include nucleic acids at their ends that span a length of the unknown nucleic acid sequence of the magnetically labeled oligonucleotide strand, and where either the analyte strand or the oligonucleotide ruler strands are labeled with at least one label; (b) transferring the mixture to a surface functionalized to couple with the at least one label; (c) applying a mechanical force to the mixture; and (d) inspecting the surface for immobilized particles.

If the analyte strand is labeled, then the oligonucleotide ruler strand that does not produce immobilized particles on the surface contains at least some of the unknown nucleic acid sequences at its end. However, if the oligonucleotide ruler strand is labeled, then the oligonucleotide ruler strand that produces immobilized particles on the surface contains at least some of the unknown nucleic acid sequences at its end. In some embodiments, a different oligonucleotide ruler strand is used to repeat steps (a)-(d) until the unknown sequence of the magnetically labeled oligonucleotide strand is determined.

In some embodiments, the present disclosure pertains to methods for determining the binding of a nucleotide to an active agent by (a) incubating a first oligonucleotide strand and a second oligonucleotide strand for hybridization in the presence of an oligonucleotide cleaving enzyme and an active agent to form a mixture, where the first and second oligonucleotide strands are complementary to one another, where at least one of the first or second oligonucleotide strands is labeled with at least one label, and where at least one of the first or second oligonucleotide strands is labeled with at least one magnetic particle to provide a magnetically labeled oligonucleotide strand; (b) transferring the mixture to a surface functionalized to couple with the at least one label; (c) applying a mechanical force to the mixture; and (d) inspecting the surface for immobilized particles.

The presence of immobilized particles indicates that the active agent binds to the at least one of the first oligonucleotide strand, the second oligonucleotide strand, or the hybridized version thereof. However, the absence of immobilized particles indicates that the active agent does not bind to the at least one of the first oligonucleotide strand, the second oligonucleotide strand, or the hybridized version thereof.

Additional embodiments of the present disclosure pertain to sample holder devices and methods of utilizing such devices. In some embodiments, the sample holder devices of the present disclosure include: (1) an incubator that includes a plurality of first wells for incubating a plurality of samples; (2) a displayer for displaying the plurality of the samples, where the displayer includes a plurality of second wells, and where a surface of each of the second wells is functionalized with a functional group that is capable of immobilizing oligonucleotide strands; and (3) a transferring apparatus that is capable of transferring the plurality of the samples from the plurality of first wells to the plurality of second wells.

Additional embodiments of the present disclosure pertain to methods of utilizing the sample holder devices of the present disclosure for transferring a plurality of samples through the following steps: (a) loading the plurality of samples into a plurality of first wells of an incubator; (b) transferring the plurality of the samples from the plurality of first wells of the incubator to a plurality of second wells of a displayer through the utilization of a transferring apparatus, where a surface of each of the second wells is functionalized with a functional group that is capable of immobilizing oligonucleotide strands; and (c) inspecting or analyzing the plurality of second wells of the displayer.

Additional embodiments of the present disclosure pertain to detection devices. In some embodiments, the detection devices of the present disclosure include: a sample holder; a light source; a voltmeter; a photodetector; and a recording device holder. In some embodiments, the detection devices of the present disclosure also include a translation stage for changing the location of the sample on the sample holder. In some embodiments, the detection devices of the present disclosure also include a mechanical frame for providing structural support to the device. In some embodiments, the detection devices of the present disclosure include a light source; a photodetector; a translation stage; a mechanical frame; and a voltmeter.

DESCRIPTION OF THE DRAWINGS

FIG. 1 depicts, in accordance with embodiments herein, several embodiments of the present disclosure.

FIG. 2 depicts, in accordance with embodiments herein, validation of force-modulated hybridization to determine nucleic acid length. FIG. 2A shows the probing of a 13-nt analyte DNA (denoted as A13) with oligonucleotide ruler strands R15-R12 in TBS buffer. FIG. 2B shows measurements by an atomic magnetometer for the four samples in FIG. 2A. FIG. 2C shows probing a 12-nt analyte DNA (denoted as A12) with oligonucleotide ruler strands R15-R12. FIG. 2D shows probing A13 and A12 in TAM10 buffer, using oligonucleotide ruler strands R15-R12. No difference was observed without force modulation. FIG. 2E shows distinguishing A13 and A12 by force modulation at 65 pN.

FIG. 3 depicts, in accordance with embodiments herein, RNA detection and label-free analysis. FIG. 3A shows a comparison of measuring A13 and A13r using the same set of DNA oligonucleotide ruler strands. FIG. 3B shows switching the functionalization from the analyte strand to the oligonucleotide ruler strands enables label-free detection.

FIG. 4 depicts, in accordance with embodiments herein, applications of the DNA ruler method. FIG. 4A depicts a sequence for determining the binding site of endonuclease DpnII. FIG. 4B shows that the fragment was measured by oligonucleotide ruler strands R15-R11. FIG. 4C shows the scheme for distinguishing the Pre and Post-translocation complexes. The ribosome position (indicated by the orange ovals) shifted by 3 nts to the right going from Pre to Post. FIG. 4D indicates that using oligonucleotide ruler strand R15' shows particle immobilization for the Pre but not for the Post. A 65 pN force was applied to the samples.

FIG. 5 depicts, in accordance with embodiments herein, resolving drug molecule-DNA binding.

FIG. 6 depicts, in accordance with embodiments herein, multiplexed analysis and quantification.

FIG. 7 depicts, in accordance with embodiments herein, a unique set of sample holders (FIG. 7A) that contains a puncher, incubator, and displayer and their use in analyzing samples (FIG. 7B).

DETAILED DESCRIPTION

Figure 1A:
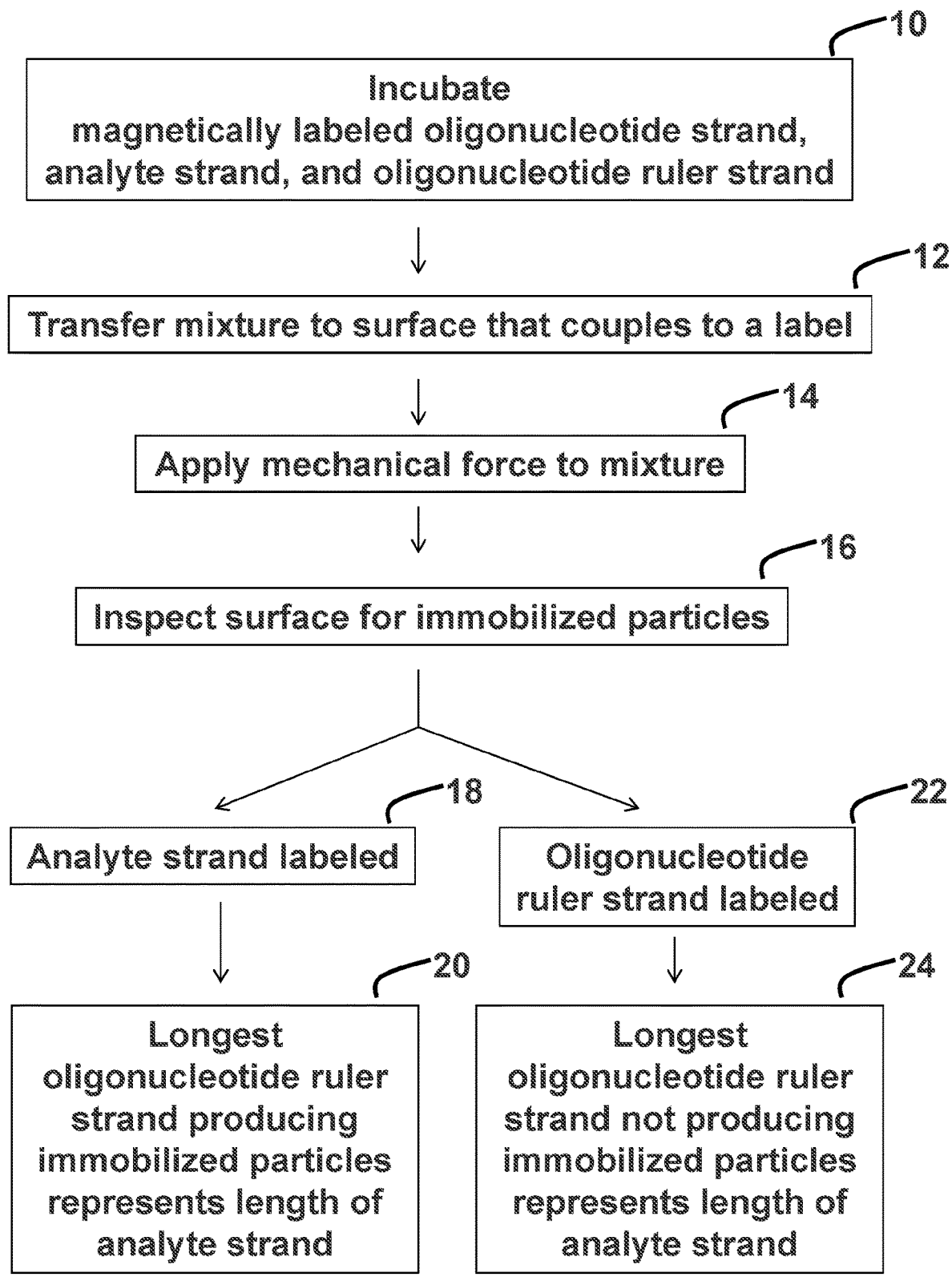
FIG. 1A provides a scheme of a method of determining the length of an analyte strand.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. The present invention is in no way limited to the methods and materials described.

The terms "polynucleotide" and "oligonucleotide," used interchangeably herein, refer generally to linear polymers of natural or modified nucleosides, including deoxyribonucleosides, ribonucleosides, alpha-anomeric forms thereof, and the like, usually linked by phosphodiester bonds or analogs thereof ranging in size from a few monomeric units, e.g. 2-4, to several hundreds of monomeric units. When a polynucleotide is represented by a sequence of letters, it will be understood that the nucleotides are in 5'→3' order from left to right. Polynucleotide as used herein also includes a basic sugar-phosphate or sugar-phosphorothioate polymers.

Measuring the exact interacting sites of nucleic acids with other biological entities is fundamental to investigating their roles in various biological functions. Examples of nucleic acid interactions include the binding sites of enzymes and inhibitors, and the dynamic positions of mRNA relative to the ribosome. Often, to determine the exact interacting site, it is essential to achieve single-nucleotide (nt) resolution. Many techniques have been developed for such measurements, such as surface-enhanced Raman spectroscopy, fluorescence resonance, circular dichroism, electrochemical methods, optical methods, plasmonic resonance, and the utilization of nanopores. In addition, high specificity methods based on thermodynamic equilibrium have been reported.

However, most of the studies used a mismatching nucleotide in the middle of a sequence to represent single-nt specificity, not at the ends. The latter is much more challenging because the difference in Gibbs free energy is substantially smaller due to duplex end breathing.

Another challenge for precisely measuring nucleic acids is the requirement of expensive instrumentation. Direct visualization of biological processes has been shown using fluorescent, magnetic, or plasmonic beads, as well as dyes and other nanomaterials. However, the key feature of high specificity has not been preserved well in comparison with sophisticated apparatus. Moreover, resolution on the length of nucleic acids has not been reported using visual or colorimetric detection.

As described herein, in accordance with the various embodiments herein, the inventors have developed a novel technology of force-modulated hybridization for DNA/RNA detection and analysis, along with the associated device and consumables. The methods and devices provided herein possesses three unique capabilities. First, they are able to measure nucleic acids with single-nucleotide length resolution, which has not been achieved with other methods. Second, they require no amplification and no expensive instrument because the changes in measuring different samples can be visually observed via the color of magnetic labels. Third, a set of specific sample holders can streamline analysis while detection devices can quantify the results when needed.

Nucleotide Length Determination

In some embodiments, the present disclosure pertains to methods of determining the length of an analyte strand. In some embodiments illustrated in FIG. 1A, the methods of the present disclosure include the following steps: (a) incubating a magnetically labeled oligonucleotide strand, the analyte strand, and one of a series of oligonucleotide ruler strands to form a mixture, where the magnetically labeled oligonucleotide strand is complementary in sequence to the analyte strand, where the series of oligonucleotide ruler strands are complementary in sequence to the magnetically labeled oligonucleotide strand and include different lengths, and where either the analyte strand or the oligonucleotide ruler strands are labeled with at least one label (step 10); (b) transferring the mixture to a surface functionalized to couple with the at least one label (step 12); (c) applying a mechanical force to the mixture (step 14); and (d) inspecting the surface for immobilized particles (step 16).

If the analyte strand is labeled, then the longest oligonucleotide ruler strand producing immobilized particles on the surface represents the length of the analyte strand (steps 18 and 20). However, if the oligonucleotide ruler strands are labeled, then the longest oligonucleotide ruler strand not producing immobilized particles represents the length of the analyte strand (steps 22 and 24). In some embodiments, a different oligonucleotide ruler strand is used to repeat steps (a)-(d) until the length of the analyte strand is determined.

Figure 1B:
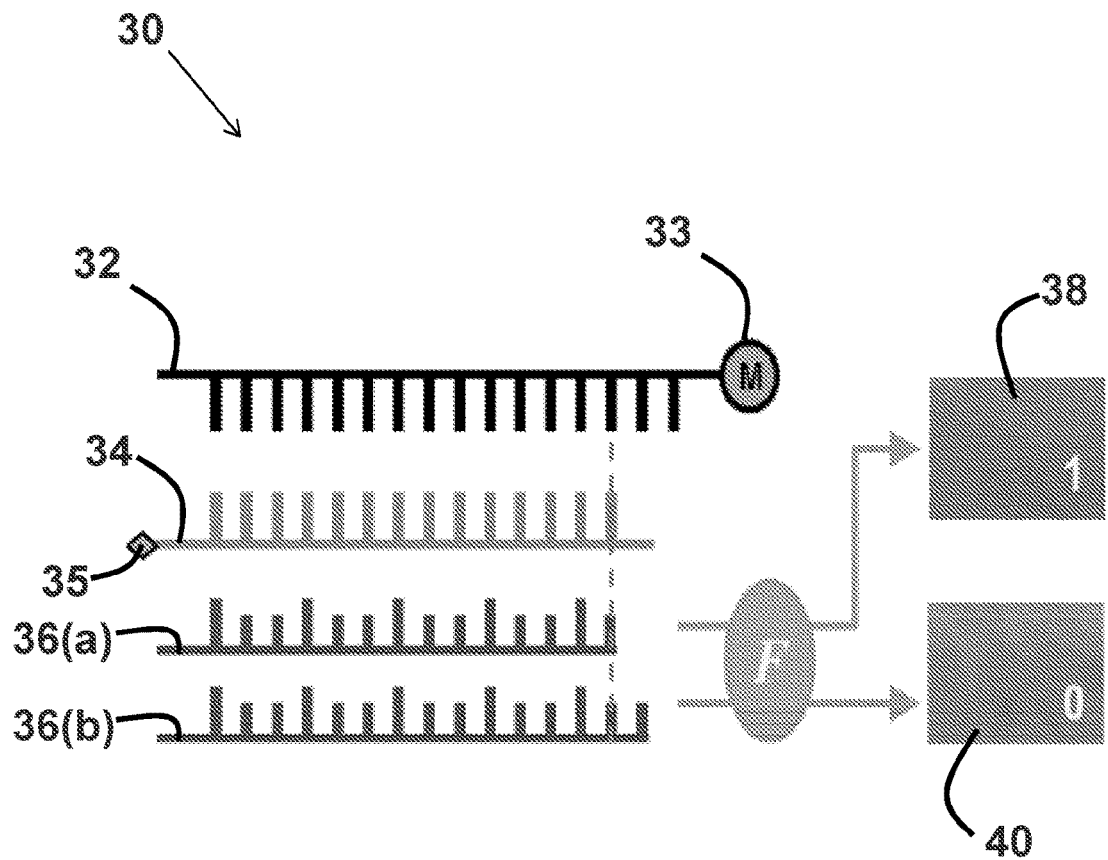
FIG. 1B illustrates a scheme for measuring the length of analyte strands. As illustrated, force-modulated hybridization will lead to the presence of immobilized particles when the oligonucleotide ruler strand is not longer than the analyte strand (top image), or to the absence of immobilized particles if the oligonucleotide ruler strand is longer (bottom image).

In a more specific embodiment illustrated in FIG. 1B, the nucleotide length determination methods of the present disclosure include a step of incubating analyte strand 34 with magnetically labeled oligonucleotide strand 32 and oligonucleotide ruler strand 36(a) or 36(b) to form a mixture 30. In this embodiment, analyte strand 34 is labeled with at least one label 35 while magnetically labeled oligonucleotide strand 32 contains magnetic particle 33.

Thereafter, mixture 30 is transferred to a surface that is functionalized to couple with label 35. Next, a mechanical force is applied to the mixture. The color of the surface is then inspected. If the surface is yellow (i.e., surface 38), then one can determine that analyte strand 34 is longer than or the same length as the oligonucleotide ruler strand (e.g., oligonucleotide ruler strand 36(a)). The basis is that, due to its length, the oligonucleotide ruler strand is not able to compete with analyte strand 34 for hybridization with magnetically labeled oligonucleotide strand 32. As such, label 35 on analyte strand 34 is able to immobilize the hybridized oligonucleotide onto a surface while magnetic particle 33 on magnetically labeled oligonucleotide strand 32 is able to generate a yellow color on the surface.

On the other hand, if the surface is colorless or not yellow (i.e., surface 40), then one can determine that the analyte strand is shorter than the oligonucleotide ruler strand (e.g., oligonucleotide ruler strand 36(b)). The basis is that, due to its longer length, the oligonucleotide ruler strand is able to compete with analyte strand 34 for hybridization with magnetically labeled oligonucleotide strand 32. As such, analyte strand 34 and magnetically labeled oligonucleotide strand 32 do not form a substantial amount of hybridized oligonucleotides that could be immobilized onto a surface through the use of label 35 on analyte strand 34. Accordingly, magnetic particle 33 on magnetically labeled oligonucleotide strand 32 is not able to generate a yellow color on the surface.

As set forth in more detail herein, the nucleotide length determination methods of the present disclosure can have numerous embodiments. In particular, various magnetically labeled oligonucleotide strands, analyte strands and oligonucleotide ruler strands may be incubated under various conditions and transferred to various types of functionalized surfaces. Moreover, various types of mechanical forces may be applied to the mixture of oligonucleotides. Surfaces may also be inspected in various manners to detect immobilized particles.

Analyte Strands

The nucleotide length determination methods of the present disclosure can be utilized to determine the length of various types of analyte strands. For instance, in some embodiments, the analyte strand is a DNA strand. In some embodiments, the analyte strand is an RNA strand.

The analyte strands of the present disclosure can include various lengths. For instance, in some embodiments, the analyte strands of the present disclosure are 10-50 nucleotides long. In some embodiments, the analyte strands of the present disclosure are 10-30 nucleotides long.

Magnetically Labeled Oligonucleotide Strands

The nucleotide length determination methods of the present disclosure may utilize various types of magnetically labeled oligonucleotide strands. For instance, in some embodiments, the magnetically labeled oligonucleotide strand is a DNA strand. In some embodiments, the magnetically labeled oligonucleotide strand is an RNA strand.

The magnetically labeled oligonucleotide strands of the present disclosure can include various lengths. For instance, in some embodiments, the magnetically labeled oligonucleotide strands of the present disclosure are 10-50 nucleotides long. In some embodiments, the magnetically labeled oligonucleotide strands of the present disclosure are 12-50 nucleotides long. In some embodiments, the magnetically labeled oligonucleotide strands of the present disclosure are 12-30 nucleotides long.

In some embodiments, the magnetically labeled oligonucleotide strands of the present disclosure have longer lengths than the analyte strand. In some embodiments, the magnetically labeled oligonucleotide strands have the same length as the analyte strand. In some embodiments, the magnetically labeled oligonucleotide strands have a shorter length than the analyte strand.

The magnetically labeled oligonucleotide strands of the present disclosure may be labeled with a magnetic particle. In some embodiments, the magnetic particles may include particles that have magnetic properties. For instance, in some embodiments, the magnetic particles include, without limitation, ferromagnetic materials, ferrimagnetic materials, and combinations thereof. In some embodiments, the magnetic particles include, without limitation, iron, nickel, cobalt, and combinations thereof.

The magnetic particles of the present disclosure can have various sizes. For instance, in some embodiments, the magnetic particles have a diameter ranging from about 10 nm to about 5000 nm. In some embodiments, the magnetic particles have a diameter ranging from about 10 nm to about 1,000 nm. In some embodiments, the magnetic particles have a diameter ranging from about 10 nm to about 500 nm.

The magnetically labeled particles of the present disclosure may be positioned at various locations on a magnetically labeled oligonucleotide strand. For instance, in some embodiments, the magnetically labeled particles are positioned at one of the ends of a magnetically labeled oligonucleotide strand. In some embodiments, the magnetically labeled particles are positioned at a central or median position on a magnetically labeled oligonucleotide strand.

Oligonucleotide Ruler Strands

The nucleotide length determination methods of the present disclosure may also utilize various types of oligonucleotide ruler strands. For instance, in some embodiments, the oligonucleotide ruler strands of the present disclosure include DNA strands, RNA strands, and combinations thereof. In some embodiments, the oligonucleotide ruler strands of the present disclosure include DNA strands. In some embodiments, the oligonucleotide ruler strands of the present disclosure include RNA strands.

In some embodiments, the oligonucleotide ruler strands of the present disclosure are complementary in sequence to the analyte strand. In some embodiments, the oligonucleotide ruler strands include oligonucleotides longer than the analyte strand. In some embodiments, the oligonucleotide ruler strands include oligonucleotides shorter than the analyte strand. In some embodiments, the oligonucleotide ruler strands include oligonucleotides the same length as the analyte strand.

Labels

The nucleotide length determination methods of the present disclosure require that either the analyte strand or the oligonucleotide ruler strand be labeled with at least one label. In some embodiments, the analyte strand is labeled with the at least one label. In such embodiments, the oligonucleotide ruler strands are not labeled with the at least one label.

In some embodiments, the oligonucleotide ruler strands are labeled with the at least one label. In such embodiments, the analyte strand is not labeled with the at least one label.

The labels of the present disclosure can include labels that could be utilized to couple an analyte strand or an oligonucleotide strand to a functionalized surface. In some embodiments, the at least one label includes, without limitation, biotin, streptavidin, digoxigenin, avidin, maleic imide, gold, proteins, nucleic acids, functional groups, and combinations thereof. In some embodiments, the at least one label is biotin. In some embodiments, the label excludes magnetic materials, such as magnetic particles. The use of additional labels can also be envisioned.

Incubation of Oligonucleotides

Various methods may be utilized to incubate magnetically labeled oligonucleotide strands, analyte strands, and an oligonucleotide ruler strand to form a mixture. For instance, in some embodiments, the incubation occurs by first incubating the magnetically labeled oligonucleotide strand and the analyte strand and then adding the oligonucleotide ruler strand. In some embodiments, the magnetically labeled oligonucleotide strand, the analyte strand and the oligonucleotide ruler strand are incubated at the same time.

Incubation can occur under various conditions. For instance, in some embodiments, incubation can occur at temperatures between 5-50° C. In some embodiments, incubation occurs at room temperature.

Incubation can also occur for various periods of time. For instance, in some embodiments, the incubation duration is between 1-300 minutes. In some embodiments, the incubation duration is about 1 minute.

Figure 1C:
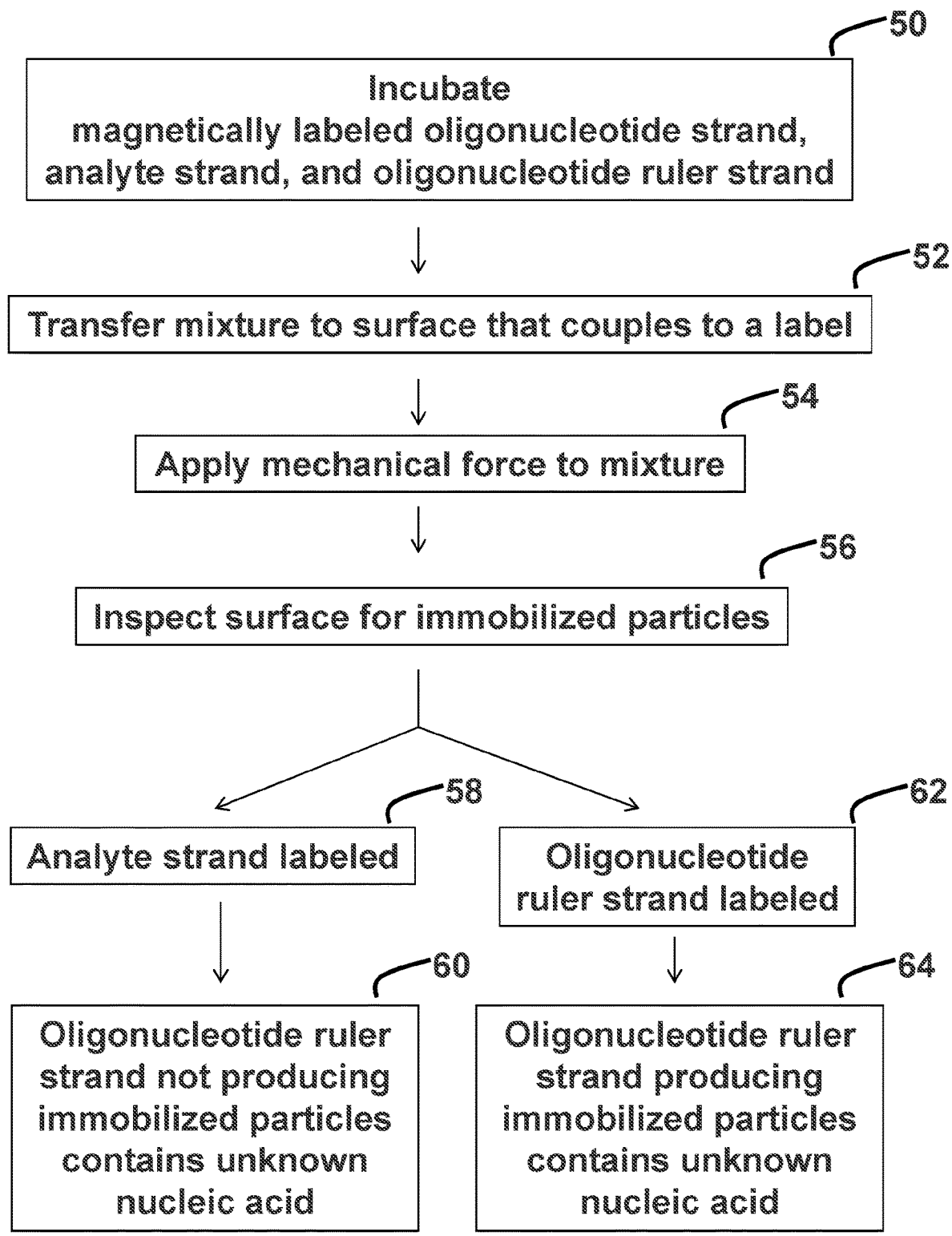
FIG. 1C provides a scheme of a method of determining unknown nucleic acid sequences.

Incubation can occur in various environments. For instance, in some embodiments, incubation can occur in a well. In some embodiments, incubation can occur in one or more wells of a sample holder device of the present disclosure (e.g., one or more of the first wells 125 of incubator 124 of sample holder device 120, as shown in FIG. 1G and described in more detail herein).

In some embodiments, the incubation step is separate and apart from the transferring step. In other embodiments, the incubation step and the transferring step occur at the same time. For instance, in some embodiments, incubation occurs when a mixture is transferred to a surface.

Transfer to Surfaces

The mixtures of the present disclosure can be transferred to various surfaces. The Surfaces of the present disclosure generally include surfaces that are functionalized to couple with the at least one label. For instance, in some embodiments, the surface is functionalized with a molecule that binds to the at least one label. In some embodiments where the at least one label is biotin, the molecule can be streptavidin. In some embodiments where the at least one label is streptavidin, the molecule can be biotin. In some embodiments where the at least one label is gold, the molecule can be a thiol.

The surfaces of the present disclosure can include various structures. For instance, in some embodiments, the surface represents a bottom portion of a well. In some embodiments, the surface includes one or more wells of a sample holder device of the present disclosure (e.g., one or more of the second wells 127 of displayer 126 of sample holder device 120, as shown in FIG. 1G and described in more detail herein). Additional structures can also be envisioned.

Various methods may also be utilized to transfer mixtures to the surfaces of the present disclosure. For instance, in some embodiments, the transfer occurs by pouring the mixture onto the surface. In some embodiments, the transfer occurs by utilizing a transferring apparatus, such as a pipette. In some embodiments, the transfer occurs by utilizing the sample transfer methods of the present disclosure (e.g., sample transfer methods illustrated in FIG. 1H and described in more detail herein).

Mechanical Forces

Various types of mechanical forces may be applied to the mixtures of the present disclosure. For instance, in some embodiments, the mechanical force includes, without limitation, gravitational force, centrifugal force, shaking force, ultrasound radiation force, magnetic force, and combinations thereof. In some embodiments, the mechanical force includes centrifugal force.

In some embodiments, the mechanical force is applied between 10 fN and 500 pN. In some embodiments, the mechanical force is applied between 1 pN and 100 pN. In some embodiments, the mechanical force is applied as a 65 pN centrifugal force.

In some embodiments, the mechanical force removes oligonucleotides from the mixture that are not specifically bound to the surface. For instance, in some embodiments, gravity force may be applied to a mixture by placing the mixture vertically to remove the nonspecifically bound oligonucleotides.

Without being bound by theory, it is envisioned that the application of a mechanical force can have various effects on the mixtures of the present disclosure. For instance, in some embodiments, the mechanical force modulates oligonucleotide hybridization. In some embodiments, the mechanical force modulates oligonucleotide hybridization between an analyte strand and a magnetically labeled oligonucleotide strand. In some embodiments, the mechanical force modulates oligonucleotide hybridization between an oligonucleotide ruler strand and a magnetically labeled oligonucleotide strand.

In some embodiments, the oligonucleotide hybridization results in the presence of immobilized particles on a surface when the analyte strand is labeled and the oligonucleotide ruler strand is not longer than the analyte strand (e.g., analyte strand 34 and oligonucleotide strand 36(*a*), as illustrated in FIG. 1B). In such embodiments, the immobilized particles represent a hybrid structure between the magnetically labeled oligonucleotide strand and the analyte strand (e.g., magnetically labeled oligonucleotide strand 32 and analyte strand 34, as illustrated in FIG. 1B).

In some embodiments, the oligonucleotide hybridization results in the absence of immobilized particles on a surface when the analyte strand is labeled and the oligonucleotide ruler strand is longer than the analyte strand (e.g., analyte strand 34 and oligonucleotide strand 36(*b*), as illustrated in FIG. 1B). In such embodiments, the oligonucleotide ruler strand hybridizes with the magnetically labeled oligonucleotide strand and prevents the labeled analyte strand from substantially hybridizing with the magnetically labeled oligonucleotide strand. As such, the labeled analyte strand is not able to produce immobilized particles on a surface.

In some embodiments, the oligonucleotide hybridization results in the presence of immobilized particles on a surface when the oligonucleotide ruler strands are labeled and the oligonucleotide ruler strand is longer than the analyte strand. In such embodiments, the immobilized particles represent a hybrid structure between the magnetically labeled oligonucleotide strand and the oligonucleotide ruler strand.

In some embodiments, oligonucleotide hybridization results in the absence of immobilized particles when the oligonucleotide ruler strands are labeled and the oligonucleotide ruler strand is shorter than or the same length as the analyte strand. In such embodiments, the unlabeled analyte strand hybridizes with the magnetically labeled oligonucleotide strand and prevents the labeled oligonucleotide ruler strand from substantially hybridizing with the magnetically labeled oligonucleotide strand. As such, the labeled oligonucleotide ruler strand is not able to produce immobilized particles on a surface.

Inspection of Surfaces

Various methods may also be utilized to inspect surfaces for immobilized particles. For instance, in some embodiments, the inspection includes, without limitation, visual inspection, measurement of light transmission, measurement by a magnetic sensor, or combinations thereof.

In some embodiments, the inspection occurs by visual inspection. In some embodiments, inspection occurs by the utilization of a device, such as the detection devices of the present disclosure (e.g., detection device 150, as shown in FIG. 1I and described in more detail herein).

In some embodiments, inspection may occur after the application of a mechanical force. In some embodiments, the surface to be inspected may be washed prior to the inspection. In some embodiments, the washing step removes non-specifically bound oligonucleotides from a surface.

In some embodiments, inspection results in the detection of immobilized particles on a surface. In some embodiments, immobilized particles are represented by a property of the magnetic particles on the magnetically labeled oligonucleotide strands. For instance, in some embodiments, the immobilized particles are represented by a yellow color on the surface (e.g., yellow color on surface 38, as shown in FIG. 1B). In some embodiments, the yellow color is derived from the magnetically labeled oligonucleotide strand, such as the magnetic particles associated with the magnetically labeled oligonucleotide strand.

Repetition of Steps

In some embodiments, the steps outlined in FIG. 1A may be repeated multiple times. For instance, in each repetition step, a different oligonucleotide ruler strand may be used to repeat steps (a)-(d) until the length of the analyte strand is determined. In some embodiments, steps (a)-(d) are repeated sequentially. In some embodiments, steps (a)-(d) are repeated in parallel or simultaneously, such as through the use of a multi-well system.

Determination of Unknown Nucleic Acid Sequences

In some embodiments, the present disclosure pertains to methods of determining an unknown nucleic acid sequence of a magnetically labeled oligonucleotide strand. In some embodiments illustrated in FIG. 1C, the methods of the present disclosure include the following steps: (a) incubating the magnetically labeled oligonucleotide strand, an analyte strand, and one of a series of oligonucleotide ruler strands to form a mixture, where the analyte strand is complementary in sequence to at least some of the known sequences of the magnetically labeled oligonucleotide strand, where the series of oligonucleotide ruler strands are complementary in sequence to the magnetically labeled oligonucleotide strand, and where the oligonucleotide ruler strands include nucleic acids at their ends that span a length of the unknown nucleic acid sequence of the magnetically labeled oligonucleotide strand, and where either the analyte strand or the oligonucleotide ruler strands are labeled with at least one label (step 50); (b) transferring the mixture to a surface functionalized to couple with the at least one label (step 52); (c) applying a mechanical force to the mixture (step 54); and (d) inspecting the surface for immobilized particles (step 56).

If the analyte strand is labeled (step 58), then the oligonucleotide ruler strand that does not produce immobilized particles on the surface contains at least some of the unknown nucleic acid sequences at its end (step 60). However, if the oligonucleotide ruler strand is labeled (step 62), then the oligonucleotide ruler strand that produces immobilized particles on the surface contains at least some of the unknown nucleic acid sequences at its end (step 64). In some embodiments, a different oligonucleotide ruler strand is used to repeat steps (a)-(d) until the unknown sequence of the magnetically labeled oligonucleotide strand is determined.

Figure 1D:
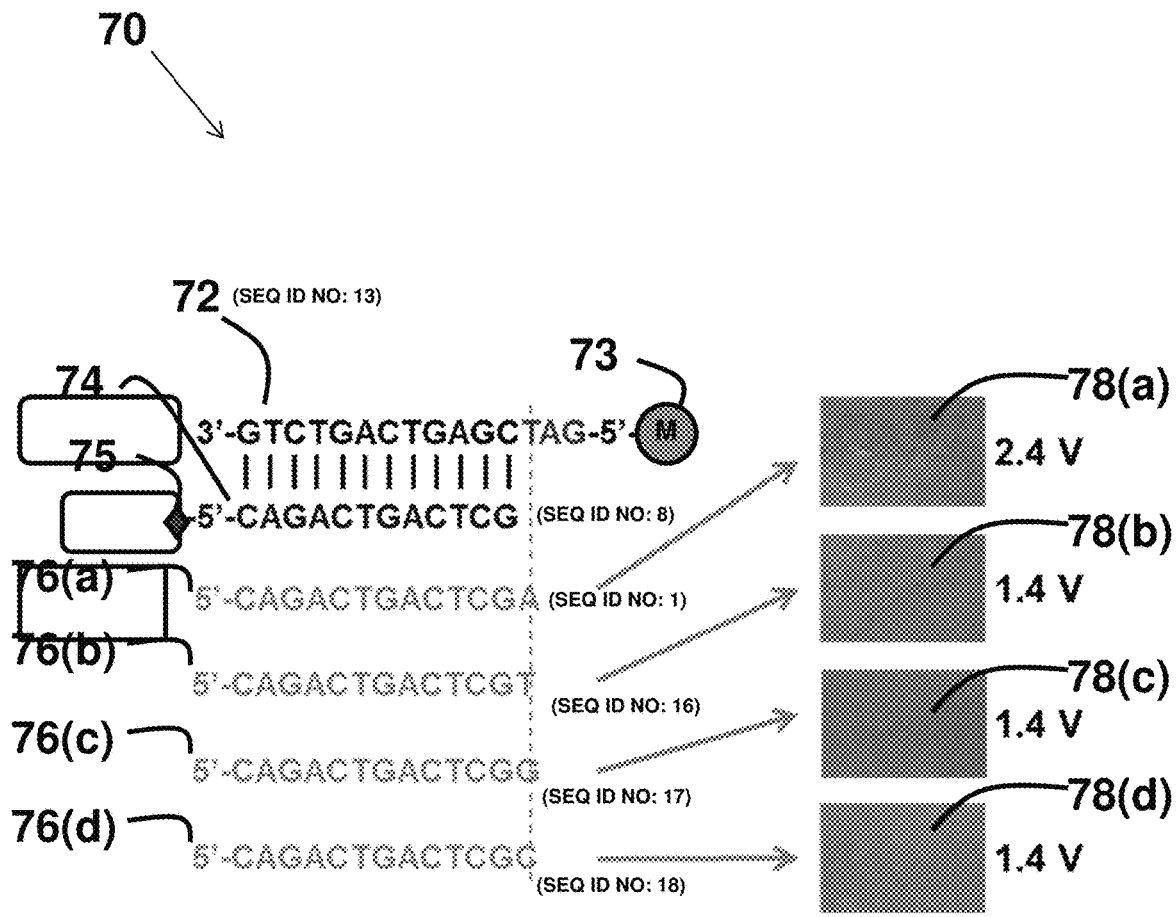
FIG. 1D provides an illustration for determining unknown nucleic acid sequences.

In a more specific embodiment illustrated in FIG. 1D, a method of determining an unknown nucleic acid sequence of magnetically labeled oligonucleotide strand 72 is disclosed. In this embodiment, magnetically labeled oligonucleotide strand 72, analyte strand 74, and one of a series of oligonucleotide ruler strands 76(*a*)-(*d*) are incubated to form a mixture 70.

As also illustrated in FIG. 1D, analyte strand 74 is complementary in sequence to at least some of the known sequences of magnetically labeled oligonucleotide strand 72. Analyte strand 74 is labeled with label 75 while magnetically labeled oligonucleotide strand 72 is labeled with magnetic particle 73. As also shown in FIG. 1D, the series of oligonucleotide ruler strands 76(*a*)-(*d*) are complementary in sequence to magnetically labeled oligonucleotide strand 72. Oligonucleotide ruler strands 76(*a*)-(*d*) also include nucleic acids at their ends that span a length of the unknown nucleic acid sequence of magnetically labeled oligonucleotide strand.

Mixture 70 is transferred to a surface functionalized to couple with label 75. Thereafter, a mechanical force is applied to the mixture. The surface is then inspected for immobilized particles. A determination can be made that oligonucleotide ruler strand 76(*a*) contains at least some of the unknown nucleic acid sequences at its end because it does not produce immobilized particles on surface 78(*a*) (as determined by the absence of a yellow color from the surface). Similarly, a determination can be made that oligonucleotide ruler strands 76(*b*)-(*d*) do not contain unknown nucleic acid sequences at their ends because they produce immobilized particles on surfaces 78(*b*)-(*d*) (as determined by the presence of a yellow color on the surface). The aforementioned steps can then be repeated with different oligonucleotide rule strands until the unknown sequence of magnetically labeled oligonucleotide strand 72 is determined.

The nucleic acid sequencing methods of the present disclosure can have numerous embodiments. For instance, as set forth previously, various magnetically labeled oligonucleotide strands, analyte strands, and oligonucleotide ruler strands may be incubated with one another under various conditions to form various mixtures. As also set forth previously, either the analyte strand or the oligonucleotide ruler strands may be labeled with various labels. Various methods set forth previously may also be utilized to transfer a mixture to various surfaces. As also set forth previously, various types of mechanical forces may be applied to a mixture. The surface may then be inspected for immobilized particles in various manners that were also set forth previously.

Additional embodiments of nucleic acid sequencing methods can also be envisioned. For instance, in some embodiments, the magnetically labeled oligonucleotide strand has a segment of known sequence followed by a segment of the unknown nucleic acid sequence. In some embodiments, the unknown nucleic acid sequence is at the end of the magnetically labeled oligonucleotide strand. In some embodiments, the unknown nucleic acid is 1-20 nucleotides long. In some embodiments, the unknown nucleic acid is 1-5 nucleotides long.

In some embodiments, the oligonucleotide ruler strands include different lengths. In some embodiments, the oligonucleotide ruler strands include oligonucleotide ruler strands that differ by only the last nucleotide. In some embodiments, the last nucleotide is complementary in sequence to an unknown nucleic acid sequence.

Active Agent-Oligonucleotide Binding Determination

Figure 1E:
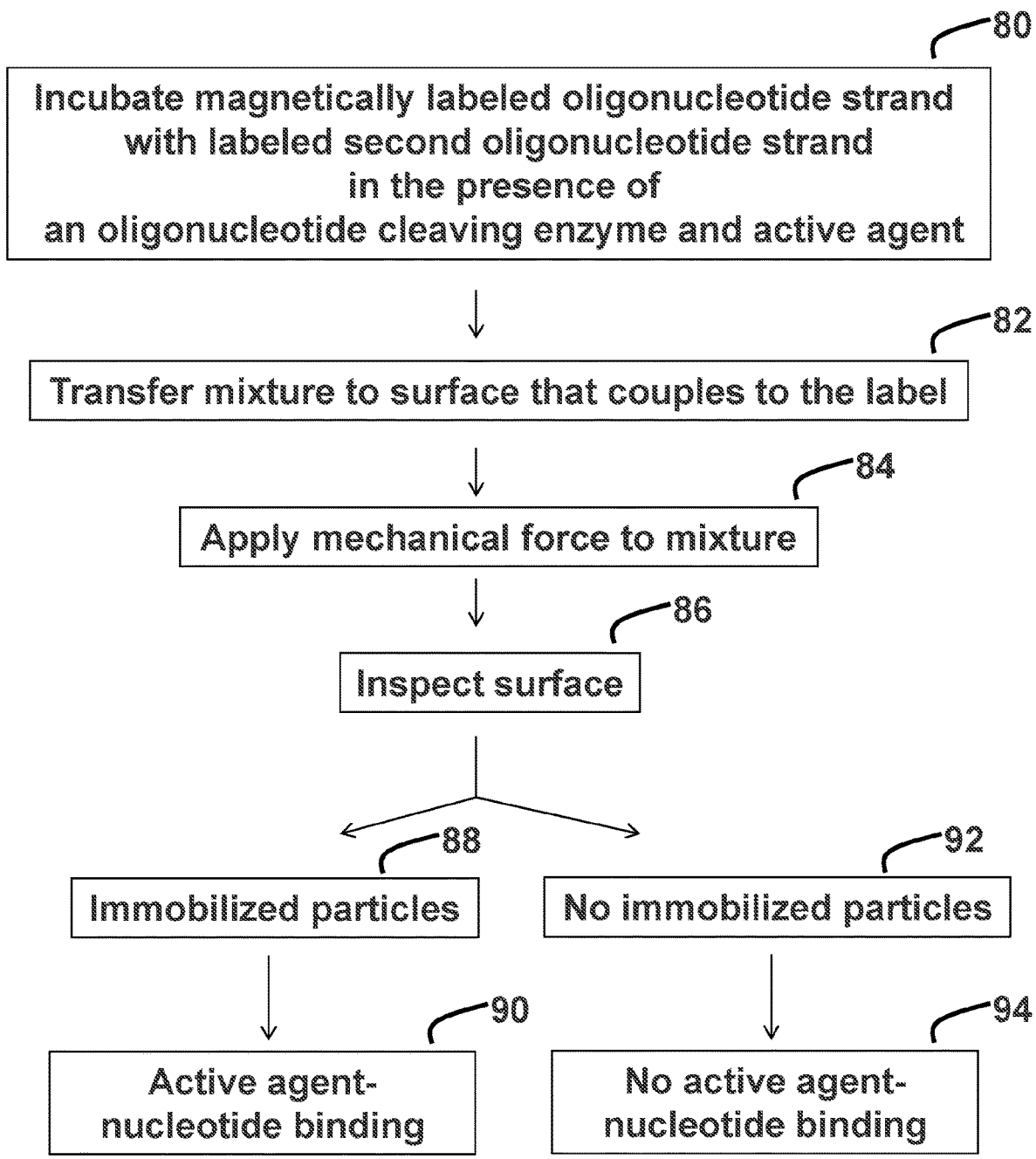
FIG. 1E provide a scheme of determining active agent-oligonucleotide binding.

In some embodiments, the present disclosure pertains to methods for determining the binding of a nucleotide to an active agent. In some embodiments illustrated in FIG. 1E, the methods of the present disclosure include the following steps: (a) incubating a first oligonucleotide strand and a second oligonucleotide strand for hybridization in the presence of an oligonucleotide cleaving enzyme and an active agent to form a mixture, where the first and second oligonucleotide strands are complementary to one another, where at least one of the first or second oligonucleotide strands is labeled with at least one label, and where at least one of the first or second oligonucleotide strands is labeled with at least one magnetic particle to provide a magnetically labeled oligonucleotide strand (step 80); (b) transferring the mixture to a surface functionalized to couple with the at least one label (step 82); (c) applying a mechanical force to the mixture (step 84); and (d) inspecting the surface for immobilized particles (step 86).

The presence of immobilized particles (step 88) indicates that the active agent binds to the at least one of the first oligonucleotide strand, the second oligonucleotide strand, or the hybridized version thereof (step 90). However, the absence of immobilized particles (step 92) indicates that the active agent does not bind to the at least one of the first oligonucleotide strand, the second oligonucleotide strand, or the hybridized version thereof (step 94).

Figure 1F:
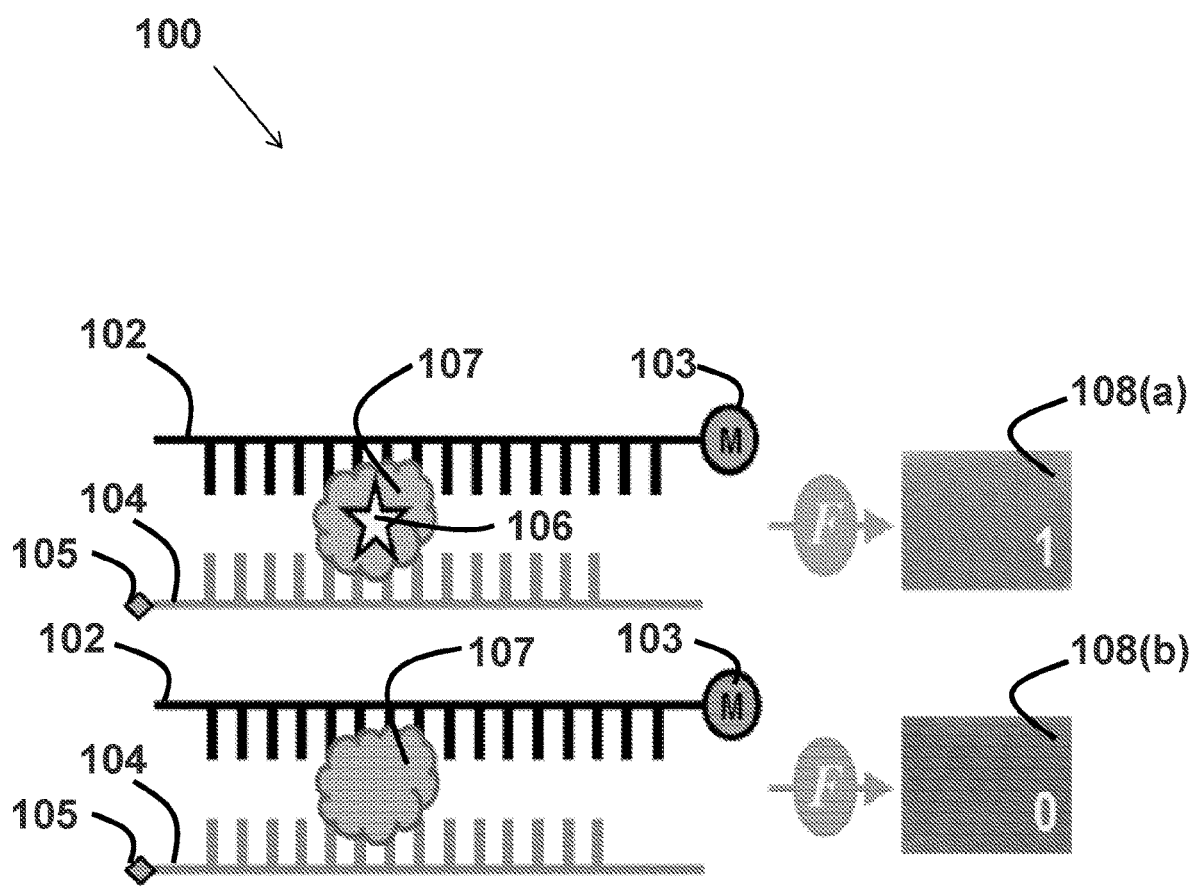
FIG. 1F illustrates a scheme for determining active agent-oligonucleotide binding, including the identification of the binding site of active agents on oligonucleotides. Immobilized particles indicate specific active agent-oligonucleotide binding at the enzyme binding site (top image). The clear sample indicated no specific active agent-oligonucleotide interactions at the enzyme binding site (bottom image).
Figure 1G:
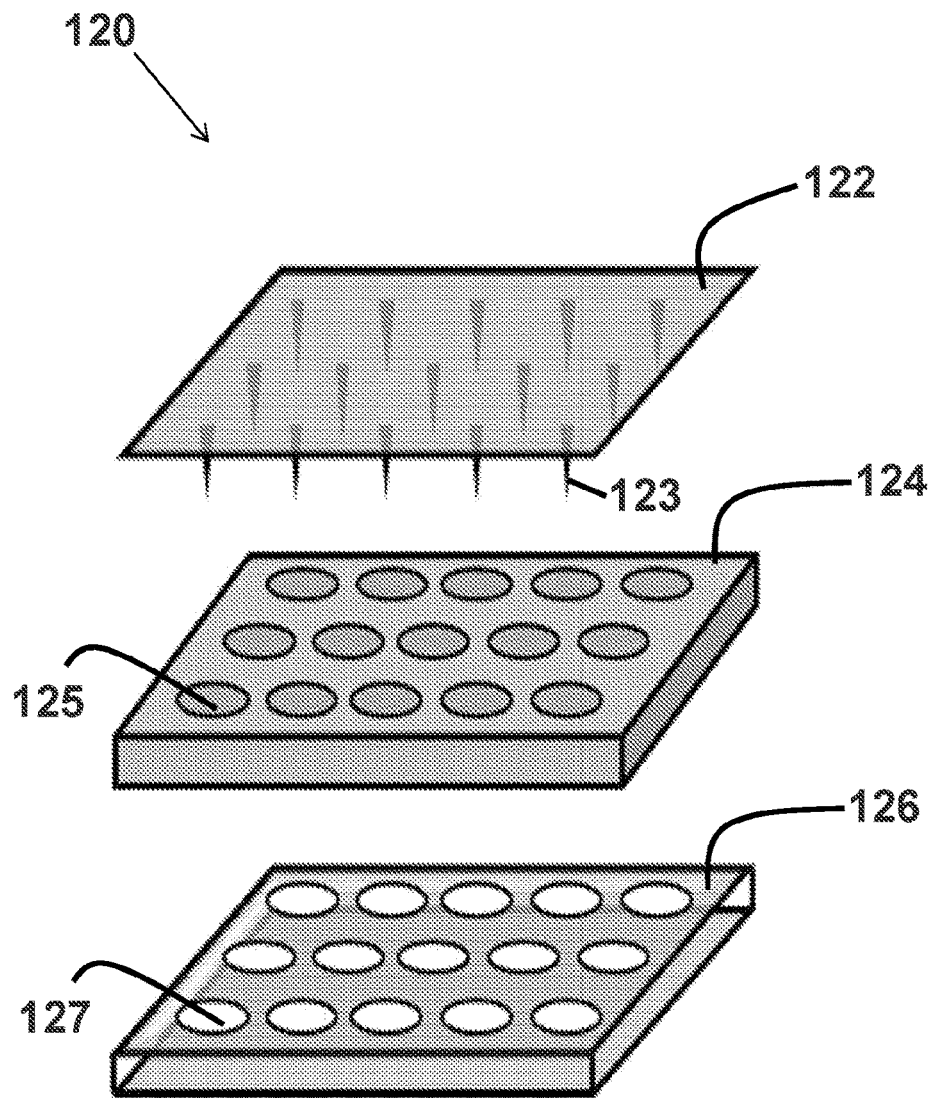
FIG. 1G shows an image of a sample holder device.
Figure 1H:
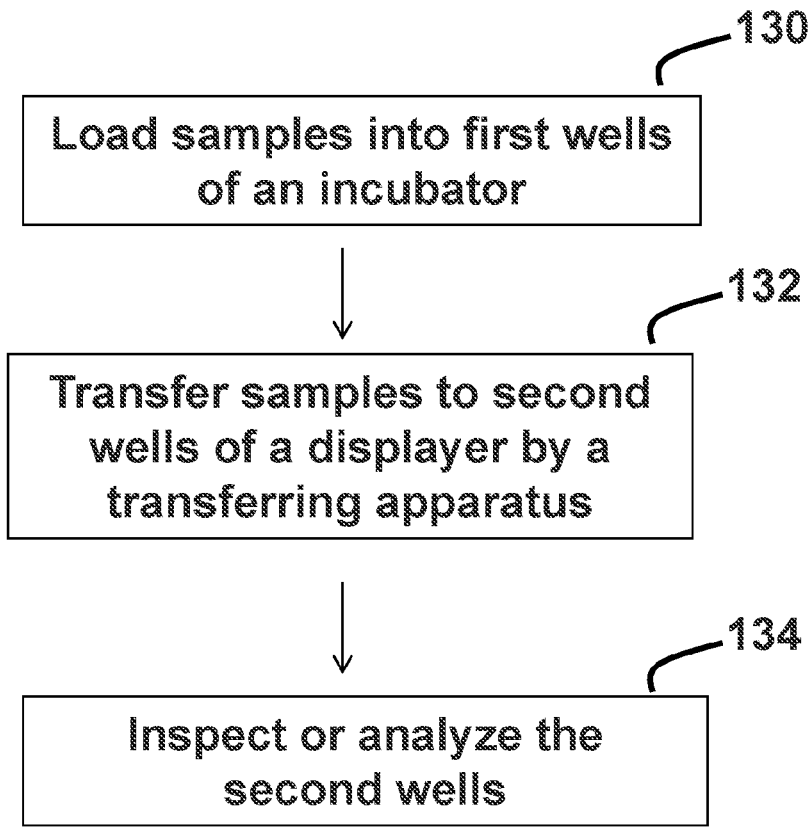
FIG. 1H illustrates a scheme related to the operation of the sample holder device.
Figure 1I:
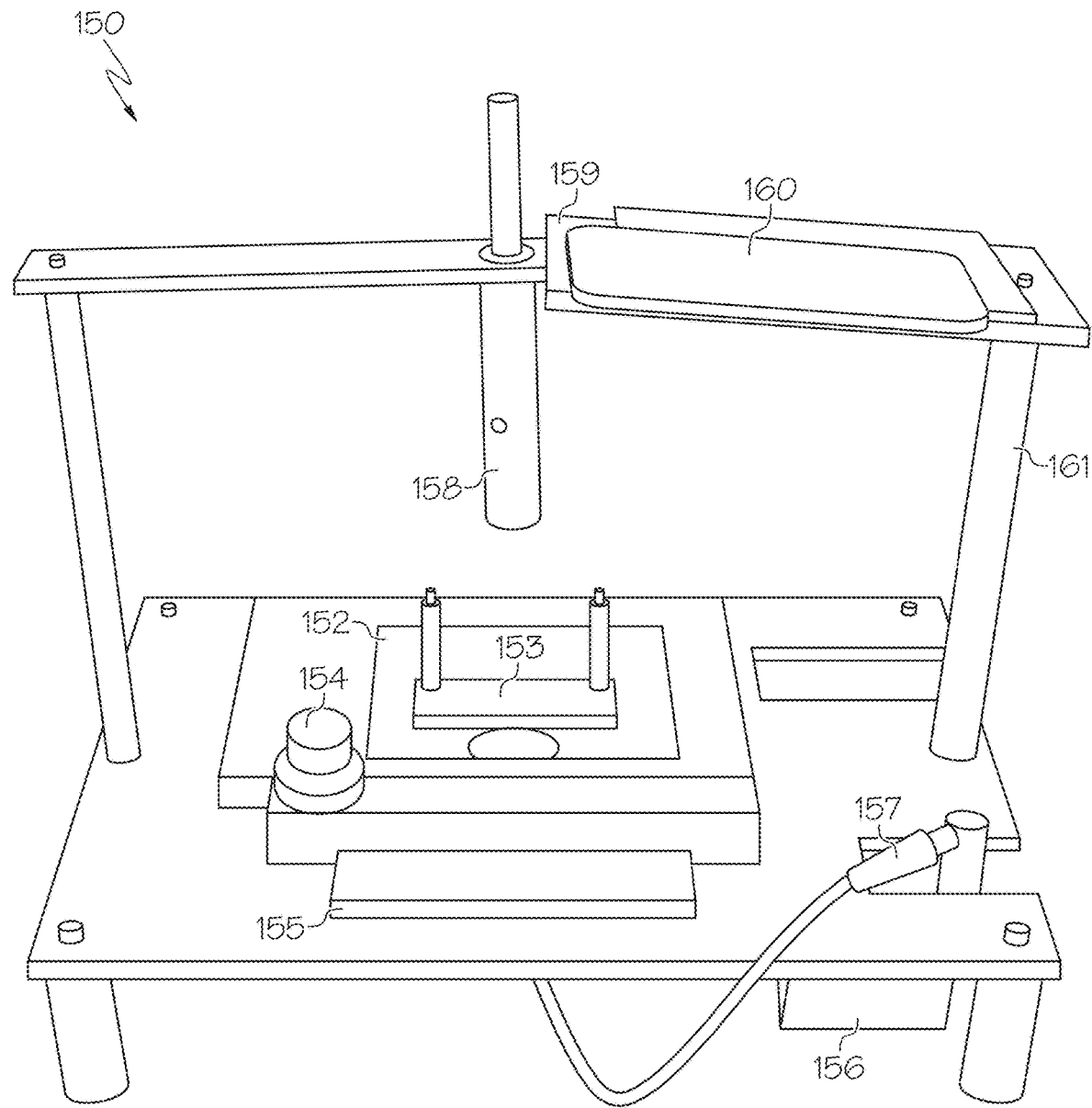
FIG. 1I shows an image of a detection device, which can be useful for multiplexed detection and quantification.

In a more specific embodiment illustrated in FIG. 1F, the methods of the present disclosure include incubating a magnetically labeled first oligonucleotide strand 102 with a second oligonucleotide strand 104 for hybridization in the presence of active agent 106 and oligonucleotide cleaving enzyme 107 to form mixture 100. In this embodiment, second oligonucleotide strand 104 is labeled with label 105 and is complementary to magnetically labeled first oligonucleotide strand 102. In addition, magnetically labeled first oligonucleotide strand 102 is labeled with magnetic particle 103.

Mixture 100 is then transferred to a surface that is functionalized to couple with label 105. A mechanical force is then applied to the mixture. The color of the surface is then inspected. If the surface is yellow (e.g., surface 108(*a*)), then a determination is made that active agent 106 binds to at least one of the magnetically labeled first oligonucleotide strand 102, the second oligonucleotide strand 104, or the hybridized version thereof. However, if the surface is colorless or not yellow (e.g., surface 108(b)), then a determination is made that the active agent does not bind to the at least one of the magnetically labeled first oligonucleotide strand, the second oligonucleotide strand, or the hybridized version thereof.

As set forth in more detail herein, the active agent-oligonucleotide binding determination methods of the present disclosure can have numerous embodiments. In particular, the methods can utilize various first oligonucleotide strands, second oligonucleotide strands, oligonucleotide cleaving enzymes, and active agents. In addition, the first and second oligonucleotide strands may be labeled with numerous types of labels and magnetic particles. In addition, the formed mixtures may be transferred to numerous surfaces. Various types of mechanical forces may also be applied to the mixture. In addition, various methods may be utilized to inspect a surface for immobilized particles in order to make an active agent-oligonucleotide binding determination.

First and Second Oligonucleotide Strands

The active agent-oligonucleotide binding determination methods of the present disclosure can utilize various first and second oligonucleotide strands. For instance, in some embodiments, each of the first and second oligonucleotide strands can include DNA strands, RNA strands, and combinations thereof. In some embodiments, the first and second oligonucleotide strands are DNA strands. In some embodiments, the first and second oligonucleotide strands are RNA strands. In some embodiments, one of the first or second oligonucleotide strands is a DNA strand while the complementary oligonucleotide strand is an RNA strand.

The first and second oligonucleotide strands of the present disclosure can include various lengths. For instance, in some embodiments, each of the first and second oligonucleotide strands of the present disclosure is 10-50 nucleotides long. In some embodiments, each of the first and second oligonucleotide strands of the present disclosure is 10-30 nucleotides long.

Labels and Magnetic Particles

The first and second oligonucleotide strands of the present disclosure may be labeled with various labels and magnetic particles in various manners. For instance, in some embodiments, the same oligonucleotide strand is labeled with the label and the magnetic particle. In some embodiments, one of the first or second oligonucleotide strands is labeled with the label while the complementary oligonucleotide strand is labeled with the magnetic particle (e.g., magnetic particle 103 on first oligonucleotide strand 102 and label 105 on second oligonucleotide strand 104, as shown in FIG. 1F).

In some embodiments, the label and the magnetic particle are on opposite termini of the first and the second oligonucleotide strands (e.g., label 105 and magnetic particle 103, as shown in FIG. 1F). In some embodiments, the label and the magnetic particle are on the same termini of the first and the second oligonucleotide strands.

Labels

Various labels may be associated with the first or second oligonucleotide strands. Suitable labels were described previously. For instance, in some embodiments, the labels can include labels that could be utilized to couple a first or second oligonucleotide strand to a functionalized surface. In some embodiments, the label includes, without limitation, biotin, streptavidin, digoxigenin, avidin, maleic imide, gold, proteins, nucleic acids, functional groups, and combinations thereof. In some embodiments, the label is biotin. In some embodiments, the label excludes magnetic materials, such as magnetic particles. The use of additional labels can also be envisioned.

Magnetic Particles

Various magnetic particles may be associated with the first or second oligonucleotide strands. Suitable magnetic particles were also described previously. For instance, in some embodiments, the magnetic particles of the present disclosure may include particles that have magnetic properties. In some embodiments, the magnetic particles include, without limitation, ferromagnetic materials, ferrimagnetic materials, and combinations thereof. In some embodiments, the magnetic particles include, without limitation, iron, nickel, cobalt, and combinations thereof.

The magnetic particles of the present disclosure can have various sizes. For instance, in some embodiments, the magnetic particles have a diameter ranging from about 10 nm to about 5000 nm. In some embodiments, the magnetic particles have a diameter ranging from about 10 nm to about 1,000 nm. In some embodiments, the magnetic particles have a diameter ranging from about 10 nm to about 500 nm.

Oligonucleotide Cleaving Enzymes

The active agent-oligonucleotide binding determination methods of the present disclosure can also utilize various oligonucleotide cleaving enzymes. For instance, in some embodiments, the oligonucleotide cleaving enzyme includes a DNA or RNA nuclease. In some embodiments, the oligonucleotide cleaving enzyme includes a DNA nuclease. In some embodiments, the oligonucleotide cleaving enzyme includes an RNA nuclease.

In some embodiments, the oligonucleotide cleaving enzyme is a restriction enzyme. In some embodiments, the restriction enzyme includes, without limitation, DpnII, EcoRI, and combinations thereof.

Active Agent

The active agent-oligonucleotide binding determination methods of the present disclosure can also utilize various active agents. For instance, in some embodiments, the active agent includes an experimental drug molecule. In some embodiments, the active agent is a molecule with undetermined or unknown nucleotide binding activities. The use of additional active agents can also be envisioned.

Incubation

Various methods may be utilized to incubate the mixtures of the present disclosure. Suitable incubation methods were described previously. For instance, in some embodiments, incubation can occur at temperatures between 5-50° C. In some embodiments, incubation occurs at room temperature.

Incubation can also occur for various periods of time. For instance, in some embodiments, the incubation duration is between 1-300 minutes. In some embodiments, the incubation duration is about 1 minute.

Incubation can occur in various environments. For instance, in some embodiments, incubation can occur in a well. In some embodiments, incubation can occur in one or more wells of a sample holder device of the present disclosure (e.g., one or more of the first wells 125 of incubator 124 of sample holder device 120, as shown in FIG. 1G and described in more detail herein).

In some embodiments, the incubation step is separate and apart from the transferring step. In other embodiments, the incubation step and the transferring step occur at the same time. For instance, in some embodiments, incubation occurs when a mixture is transferred to a surface.

Transfer to Surfaces

The mixtures of the present disclosure can be transferred to various surfaces. The Surfaces of the present disclosure generally include surfaces that are functionalized to couple with the at least one label. Suitable surfaces were described previously. For instance, in some embodiments, the surface is functionalized with a molecule that binds to the at least one label. In some embodiments where the at least one label is biotin, the molecule can be streptavidin. In some embodiments where the at least one label is streptavidin, the molecule can be biotin.

The surfaces of the present disclosure can include various structures. For instance, in some embodiments, the surface represents a bottom portion of a well. Additional structures can also be envisioned. In some embodiments, the surface includes one or more wells of a sample holder device of the present disclosure (e.g., one or more of the second wells 127 of displayer 126 of sample holder device 120, as shown in FIG. 1G and described in more detail herein). Additional structures can also be envisioned.

Various methods may also be utilized to transfer mixtures to the surfaces of the present disclosure. For instance, in some embodiments, the transfer occurs by pouring the mixture onto the surface. In some embodiments, the transfer occurs by utilizing a transferring apparatus, such as a pipette. In some embodiments, the transfer occurs by utilizing the sample transfer methods of the present disclosure (e.g., sample transfer methods illustrated in FIG. 1H and described in more detail herein).

Mechanical Forces

Various types of mechanical forces may be applied to the mixtures of the present disclosure. Suitable mechanical forces were described previously. For instance, in some embodiments, the mechanical force includes, without limitation, gravitational force, centrifugal force, shaking force, ultrasound radiation force, magnetic force, and combinations thereof. In some embodiments, the mechanical force includes centrifugal force.

In some embodiments, the mechanical force is applied between 10 fN and 500 pN. In some embodiments, the mechanical force is applied between 1 pN and 100 pN. In some embodiments, the mechanical force is applied as a 65 pN centrifugal force.

In some embodiments, the mechanical force removes oligonucleotides from the mixture that are not specifically bound to the surface. For instance, in some embodiments, gravity force may be applied to a mixture by placing the mixture vertically to remove the nonspecifically bound oligonucleotides.

Without being bound by theory, it is envisioned that the application of a mechanical force can have various effects on the mixtures of the present disclosure. For instance, in some embodiments, the mechanical force modulates oligonucleotide hybridization. In some embodiments, the mechanical force modulates oligonucleotide hybridization between a first oligonucleotide strand and a second oligonucleotide strand.

In some embodiments, the oligonucleotide hybridization results in the presence of immobilized particles on a surface when the active agent prevents the oligonucleotide cleaving enzyme from cleaving the first and second oligonucleotides. In such embodiments, the immobilized particles represent a hybrid structure between the first oligonucleotide strand and the second oligonucleotide strand (e.g., oligonucleotide strand 102 and second oligonucleotide strand 104, as illustrated in FIG. 1F). The label on the first or second oligonucleotide strand immobilizes the hybrid structure onto a surface while the magnetic particle on the first or second oligonucleotide strand is utilized to detect the immobilized particle.

In some embodiments, the methods of the present disclosure result in the absence of immobilized particles on a surface when the active agent cannot prevent the oligonucleotide cleaving enzyme from cleaving the first and second oligonucleotides. In such embodiments, the first and/or second oligonucleotide are cleaved by the active agent. As such, the label on the first or second oligonucleotide strand is not able to immobilize the hybrid structure onto a surface to form immobilized particles.

Inspection of Surfaces

Various methods may also be utilized to inspect surfaces for immobilized particles. Suitable inspection methods were also described previously. For instance, in some embodiments, the inspection includes, without limitation, visual inspection, measurement of light transmission, measurement by a magnetic sensor, or combinations thereof.

In some embodiments, the inspection occurs by visual inspection. In some embodiments, inspection occurs by the utilization of a device, such as the detection devices of the present disclosure (e.g., detection device 150, as shown in FIG. 1I and described in more detail herein).

In some embodiments, inspection may occur after the application of a mechanical force. In some embodiments, the surface to be inspected may be washed prior to the inspection. In some embodiments, the washing step removes non-specifically bound oligonucleotides from a surface.

In some embodiments, inspection results in the detection of immobilized particles on a surface. In some embodiments, immobilized particles are represented by a property of the magnetic particles on the first or second oligonucleotides. For instance, in some embodiments, the immobilized particles are represented by a yellow color on the surface (e.g., yellow color on surface 108(*a*), as shown in FIG. 1F).

Determining Active Agent Binding Site on Oligonucleotides

The active agent-oligonucleotide binding determination methods of the present disclosure can have various applications. For instance, in some embodiments, such methods can be utilized as an active agent screening assay for identifying active agents that bind to a nucleotide. In some embodiments, the active agent binding site represents the enzyme binding site. In some embodiments, no active agent is present for control experiments.

Sample Holder Devices

Additional embodiments of the present disclosure pertain to sample holder devices and methods of utilizing such devices. In some embodiments, the sample holder devices of the present disclosure include: (1) an incubator that includes a plurality of first wells for incubating a plurality of samples; (2) a displayer for displaying the plurality of the samples, where the displayer includes a plurality of second wells, and where a surface of each of the second wells is functionalized with a functional group that is capable of immobilizing oligonucleotide strands; and (3) a transferring apparatus that is capable of transferring the plurality of the samples from the plurality of first wells to the plurality of second wells.

A more specific embodiment of a sample holder device is illustrated in FIG. 1G as sample holder device 120. In this embodiment, sample holder device 120 includes: (1) an incubator 124 that includes a plurality of first wells 125 for incubating a plurality of samples; (2) a displayer 126 for displaying the plurality of the samples, where the displayer includes a plurality of second wells 127, and where a surface of each of the second wells is functionalized with a functional group that is capable of immobilizing oligonucleotide strands; and (3) a transferring apparatus 122, that is capable of transferring the plurality of the samples from the plurality of first wells 125 to the plurality of second wells 127.

As set forth in more detail herein, the sample holder devices of the present disclosure can have numerous embodiments. For instance, in some embodiments, the plurality of second wells are superimposable on the plurality of first wells. In some embodiments, the surface region of the plurality of second wells is the bottom portion on each of the plurality of the second wells.

Moreover, the surfaces of the plurality of second wells may be functionalized with various functional groups. In some embodiments, the functional groups include functional groups that are suitable for binding to the labels that were described previously, such as biotin. In some embodiments, the functional groups are a small molecule. In some embodiments, the functional groups are streptavidin.

The sample holder devices of the present disclosure can also include various transferring apparatus. For instance, in some embodiments, the transferring apparatus is in the form of a perforator (e.g., perforator 122 shown in FIG. 1G). In some embodiments, the perforator is capable of breaking or perforating a surface of the plurality of first wells so that the plurality of the samples from the plurality of first wells are transferred to the plurality of second wells. In some embodiments, the perforator includes a matrix of sharp tips (e.g., sharp tips 123 shown in FIG. 1G) at positions corresponding to the plurality of first wells.

In some embodiments, the transferring apparatus includes a sample transport system. In some embodiments, the sample transport system is capable of transporting the plurality of the samples from the plurality of first wells to the plurality of second wells. In some embodiments, the sample transport system includes a multi-head pipette system. In some embodiments, the sample transport system includes a robotic arm.

The sample holder devices of the present disclosure can be in various forms. For instance, in some embodiments, the sample holder devices of the present disclosure can be in the form of a kit for oligonucleotide hybridization. In some embodiments, the kit is utilized to practice the methods of the present disclosure, such as methods of determining the length of an analyte strand, methods of determining an unknown nucleic acid sequence of a magnetically labeled oligonucleotide strand, and methods for determining the binding of a nucleotide to an active agent.

Methods of Transferring Samples

Additional embodiments of the present disclosure pertain to methods of utilizing the sample holder devices of the present disclosure for transferring a plurality of samples. In some embodiments illustrated in FIG. 1H, the methods of the present disclosure include the following steps: (a) loading the plurality of samples into a plurality of first wells of an incubator (step 130); (b) transferring the plurality of the samples from the plurality of first wells of the incubator to a plurality of second wells of a displayer through the utilization of a transferring apparatus, where a surface of each of the second wells is functionalized with a functional group that is capable of immobilizing oligonucleotide strands (step 132); and (c) inspecting or analyzing the plurality of second wells of the displayer (step 134).

In some embodiments where the transferring apparatus includes a perforator, the transferring step can include utilizing the perforator to break or perforate the surface of the plurality of first wells so that the plurality of the samples from the plurality of first wells are transferred to the plurality of second wells. In such embodiments, the methods of the present disclosure can also include a step of aligning the displayer below the incubator prior to breaking or perforating, such that the aligning places the plurality of second wells directly below the plurality of corresponding first wells.

In some embodiments where the transferring apparatus includes a sample transport system, the transfer step can include a step of transporting the plurality of the samples from the plurality of first wells to the plurality of second wells. In some embodiments, the transport can occur by the utilization of a multi-head pipette system. In some embodiments, the transport can occur by the utilization of a robotic arm.

In some embodiments, the sample transfer methods of the present disclosure may also include a step of applying mechanical force to the plurality of second wells. In some embodiments, the mechanical force is applied prior to inspecting or analyzing the second wells. In some embodiments, the mechanical force is applied prior to transferring the samples from the plurality of the first wells to the plurality of the second wells. In some embodiments, the mechanical force is applied after transferring the samples from the plurality of the first wells to the plurality of the second wells.

Various types of mechanical forces can be applied to the samples. Suitable mechanical forces were described previously. For instance, in some embodiments, the mechanical force is in the form of gravitational force, centrifugal force, shaking force, ultrasound radiation force, magnetic force, and combinations thereof.

Detection Devices

Additional embodiments of the present disclosure pertain to detection devices. In some embodiments, the detection devices of the present disclosure include: a sample holder; a light source; a voltmeter; a photodetector; and a recording device holder. In some embodiments, the detection devices of the present disclosure also include a translation stage for changing the location of the sample on the sample holder. In some embodiments, the detection devices of the present disclosure also include a mechanical frame for providing structural support to the device. In some embodiments, the detection devices of the present disclosure include a light source; a photodetector; a translation stage; a mechanical frame; and a voltmeter.

An example of a detection device is illustrated as detection device 150 in FIG. 1I. In this embodiment, detection device 150 includes sample holder 152 for holding sample 153; translation stage 154 for changing the location of sample 153 on sample holder 154; photodetector 155 beneath sample holder 152; voltmeter 156 connected to photodetector 155 through wiring 157; light source 158 positioned above sample holder 152; recording device holder 159 for holding recording device 160; and mechanical frame 161 for providing structural support to detection device 150. As set forth in more detail herein, the detection devices of the present disclosure can have numerous embodiments.

Sample Holders

The detection devices of the present disclosure can include various sample holders. For instance, in some embodiments, the sample holder is a multiplexed sample holder. In some embodiments, the multiplexed sample holder is capable of holding a plurality of samples, such as samples positioned in a plurality of wells (e.g., samples in a plurality of second wells 127 of displayer 126, as shown in FIG. 1G).

Light Source

The detection devices of the present disclosure can also include various light sources. For instance, in some embodiments, the light source includes a laser pointer. In some embodiments, the light source includes a laser diode.

Light sources may be positioned on various regions of a detection device. For instance, in some embodiments, the light source is positioned above a sample holder (e.g., light source 158 positioned above sample holder 152, as shown in FIG. 1I).

Photodetector

The detection devices of the present disclosure can also include various photodetectors. For instance, in some embodiments, the photodetectors include photodiodes. The use of additional photodetectors can also be envisioned.

The photodetectors of the present disclosure can be positioned at various locations of a detection device. For instance, in some embodiments, a photodetector may be beneath a sample holder (e.g., photodetector 155 beneath sample holder 152, as shown in FIG. 1I). In some embodiments, the photodetector may be connected to a voltmeter, such as through a wiring (e.g., photodetector 155 connected to voltmeter 156 through wiring 157).

Recording Device Holders

The detection devices of the present disclosure can also include various recording device holders. Recording device holders generally refer to objects that are capable of holding recording devices, such as cameras, video recorders, and smartphones.

In some embodiments, recording device holders have a structure that is capable of supporting the recording device (e.g., recording device holder 159 shown in FIG. 1I). In some embodiments, the recording device holders are positioned above a sample holder such that the recording device is capable of recording or taking photographs of the sample (e.g., recording device holder 159 above sample holder 152).

Translation Stages

The detection devices of the present disclosure can also include various translation stages. Translation stages generally refer to structures that are capable of changing the location of a sample on a sample holder (e.g., translation stage 154 for changing the location of sample 153 on sample holder 152, as shown in FIG. 1I).

In some embodiments, the translation stage is a one-dimensional manual stage. In some embodiments, the translation stage is a one-dimensional manual automated stage. In some embodiments, the translation stage is a two-dimensional manual stage (e.g., translation stage 154 shown in FIG. 1I). In some embodiments, the translation stage is a two-dimensional automated stage.

Mechanical Frame

The detection devices of the present disclosure can also include various mechanical frames. Mechanical frames generally refer to objects that are capable of providing structural support to the detection devices of the present disclosure. In some embodiments, the mechanical frames of the present disclosure may be in the form of a table (e.g., mechanical frame 161 shown in FIG. 1I). Additional mechanical frame structures can also be envisioned.

Operation of Detection Devices

The detection devices of the present disclosure may be operated in various manners and for various purposes. For instance, in some embodiments that refer to detection device 150 in FIG. 1I for exemplary purposes only, sample 153 is placed on sample holder 152. Translation stage 154 can then be utilized to change the location of sample 153 on sample holder 154. For instance, translation stage 154 can be utilized to place sample 153 directly beneath light source 158.

Thereafter, light source 158 transmits light to sample 153. Photodetector 155 then transmits the transmitted light to voltmeter 156 through wiring 157. Moreover, recording device 160 on recording device holder 159 may record or take photos of sample 153. In addition, mechanical frame 161 provides structural support to detection device 150 throughout the aforementioned processes.

As such, the detection devices of the present disclosure can have numerous applications. For instance, in some embodiments, the detection devices of the present disclosure may be useful for multiplexed detection and quantification. In some embodiments, the detection devices of the present disclosure may be utilized to analyze samples in the sample holder devices of the present disclosure (e.g., sample device holder 120 shown in FIG. 1G). In some embodiments, the detection devices of the present disclosure may be utilized to practice the methods of the present disclosure, such as methods of determining the length of an analyte strand, methods of determining an unknown nucleic acid sequence of a magnetically labeled oligonucleotide strand, and methods for determining the binding of a nucleotide to an active agent.

Applications and Advantages

The devices and methods of the present disclosure have numerous applications and advantages. For instance, the nucleotide length determination methods of the present disclosure are capable of measuring the exact length of nucleic acids. Such capability can find numerous applications in biosensing, such as miRNA detection, as well as fundamental research on DNA and RNA functions.

Likewise, the active agent-oligonucleotide binding determination methods of the present disclosure can be used to precisely determine the binding site of drug molecules interacting with nucleic acids with high-throughput capacity.

Moreover, the methods of the present disclosure are versatile and tunable for use in a wide range of biological conditions. For instance, in some embodiments, force-modulated hybridization conditions can be experimentally determined for each and every system that contains different components (e.g., buffers, ion species, ion concentrations, and types of oligonucleotides).

Moreover, the devices and methods of the present disclosure can eliminate the need for expensive apparatus because single-nucleotide resolution can be observed directly by the naked eye in some embodiments. If desired, quantification can then be achieved by utilizing readily accessible detection devices for measuring light transmission, such as the detection devices of the present disclosure. Moreover, a special set of sample holders, such as the sample holder devices of the present disclosure, can be designed to facilitate analysis.

As such, depending on a desired application, various aspects of the present disclosure can be combined in various manners. For instance, in some embodiments, the present disclosure can be directed to a kit to a method and device for precisely visualizing a nucleic acid's length and function. In some embodiments, the kit can be useful for practicing the inventive method of precisely visualizing a nucleic acid's length and function, and/or measuring drug-DNA binding.

In some embodiments, the kit is an assemblage of materials or components, including at least one of methods and devices of the present disclosure. Thus, in some embodiments, the kit can contain a composition including the oligonucleotides of the present disclosure, as described above.

The exact nature of the components configured in the kit depends on its intended purpose. For example, some embodiments may be configured for the purpose of treating a disease. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to precisely visualize a nucleic acid's length and function and/or determine drug-nucleic acid binding. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form. In some embodiments, the components can be provided at room, refrigerated or frozen temperatures. In some embodiments, the components are typically contained in suitable packaging material(s).

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Force Modulated DNA Hybridization Method

In this Example, Applicants describe a force-modulated DNA hybridization method that can precisely determine the length of nucleic acids with single-nucleotide resolution and directly visualize the position of nucleic acids during their various biological functions. The method disclosed herein is robust, accurate, versatile, and requires no expensive apparatus.

The primary scheme contains a magnetically labeled DNA strand and a series of complementary strands of different lengths. The length of the nucleic acid to be analyzed can be accurately determined by force-modulated competitive hybridization. The detection can be achieved by atomic magnetometers, optical transmission, or visually with no apparatus.

To determine the exact binding site of drugs on nucleic acids, a derived scheme contains a magnetically labeled DNA and its complementary strand, in the presence of the drug to be analyzed and a DNA-cleaving enzyme. The binding site of the drug can be precisely determined by force modulation following surface immobilization.

Example 1.1. Force Modulated Competitive Hybridization

FIG. 1B can be utilized to illustrate the scheme of a force modulated competitive hybridization system 30. A magnetically labeled DNA strand 32 is designed to be complementary to the analyte strand 34 to be measured, but with several excessive nucleotides. Then a series of DNA rulers 36 are respectively added to the sample containing the two previous strands. Due to the competitive thermodynamic binding, two different scenarios will occur. If the oligonucleotide ruler strand is shorter than or as long as the analyte strand, the analyte strand and magnetically labeled oligonucleotide strand will form duplexes, allowing immobilization of the magnetic particle. Consequently he sample will appear yellow, denoted as "1" for the image 38. If the oligonucleotide ruler strand is longer than the analyte strand, the thermodynamically favored ruler-magnetically labeled oligonucleotide strand hybridization will not be able to immobilize the magnetic particle because of the absence of a functional group on the oligonucleotide ruler strands. Consequently the sample will be clear, denoted as "0" for the image 40. The samples can be distinguished by naked eye and the images can be recorded by a smart phone.

Example 1.2. Drug-Nucleotide Binding

FIG. 1D can be utilized to illustrate a system 100 for measuring drug-DNA binding. A magnetically labeled DNA strand 102 is hybridized with its complementary strand 104, in the presence of a drug molecule 106 and a DNA-cleaving enzyme 107. If the drug binds with the DNA specifically at the location of the enzyme, the enzyme will not be able to cleave the duplex. Consequently, the magnetic particles will be able to be immobilized on the surface via the biotin 105 on complementary strand 104, showing yellowish color in image 108(a) and being assigned as "1". If the drug does not bind specifically at the enzyme's site on the DNA, the duplex will be cleaved. Thus, the magnetic particles will not be able to bind with the surface because of the absence of a functional group (such as biotin 105 shown in FIG. 1D) to interact with the matching functional group on the surface, showing as clear and being assigned as "0" in image 108(b).

Example 1.3. Measuring Nucleic Acid Length with Single-Nucleotide Resolution

FIG. 2A shows the proof-of-principle results of measuring an analyte strand A13, which contains 13 complementary nucleotides (nts) with the magnetically labeled oligonucleotide strand. The experiments were performed in the TBS buffer. The oligonucleotide ruler strand length went from 15, 14, 13, to 12 nts complementary to the magnetically labeled oligonucleotide strand, denoted as R15, R14, R13, and R12, respectively. Gravity force was applied on the samples by placing them vertically to remove the nonspecifically bound magnetic particles. The buoyant mass of the magnetic particles has been measured to be $4.6 \times 10^{-15}$ kg, resulting a gravity of 45 fN. Both R15 and R14 showed no immobilized particles, thus "0" was assigned; R13 and R12 showed particles on the surface, indicated by "1" on the images.

The absence or existence of immobilized magnetic particles were confirmed using an atomic magnetometer (FIG. 2B). High magnetic signal of 100 pT was obtained for the "1" images using R13 and R12, whereas very low signal was obtained for the "0" images using R15 and R14. The "0" to "1" transition occurred at R13, indicating the analyte strand to be 13-nt length. When the analyte strand was changed to be 12-nt complementary to the magnetically labeled oligonucleotide strand (denoted as A12), such transition occurred at R12 (FIG. 2C). Therefore, the results indicated that DNA rulers can distinguish DNAs with single-nt length difference.

The basis of the DNA ruler system is the thermodynamic equilibrium between two competitive hybridizations, which is difficult to predict and varies with different biological conditions. This problem is solved by applying an adjustable mechanical force on the sample after surface immobilization.

In FIG. 2D, the same ruler systems were tested in the TAM$_{10}$ buffer. When only gravity was applied, A13 and A12 showed the same pattern, in which both transitions took place at R14. The same result was obtained even when the samples were heated to 75° C. This means without appropriate force modulation or simply using heating, single-nt resolution cannot be achieved. However, when a 65 pN centrifugal force was applied, A13 and A12 were distinguished, with transitions at oligonucleotide ruler strands of their respective lengths (FIG. 2E). The force value is just above the approximate dissociation force of single 13-bp DNA duplexes. The requirement of force indicates that R14 replacing A13 in TAM$_{10}$ is not as efficient as in TBS.

The method can also determine the length of RNAs. FIG. 3A compares measurements of A13 and its RNA analog, A13r, using DNA rulers R15-R12. The "0" to "1" transition occurred at R12 for the RNA A13r, consistent with the fact that DNA-DNA duplex is slightly more stable than the corresponding RNA-DNA duplex. In other words, the small difference between the two duplexes was successfully revealed.

A slight adjustment of the scheme can achieve label-free detection. Here, the biotin label was placed on the oligonucleotide ruler strands, leaving the analyte strand label-free (FIG. 3B). The transition is therefore reversed to "1" to "0", compared to the original scheme in FIG. 1B. Images shown were using R12 (top) and R13 (bottom) to probe A13.

The sequences used above and throughout this disclosure are listed in Table 1.

TABLE 1

Sequences of the DNAs and RNAs used in this disclosure.

| Name | Sequence (from 5' to 3') |
| --- | --- |
| A13 | Bio/CAG ACT GAC TCG A$^a$ (SEQ ID NO: 15) |
| A12 | Bio/CAG ACT GAC TCG (SEQ ID NO: 2) |
| A13r | Bio/rCrArG rArCrT rGrArC rTrCrG rA$^b$ (SEQ ID NO: 1) |
| Magnetically labeled oligonucleotide strand | A$_{25}$/GAT CGA GTC AGT CTG$^c$ (SEQ ID NO: 4) |
| R15 | CAG ACT GAC TCG ATC (SEQ ID NO: 5) |
| R14 | CAG ACT GAC TCG AT (SEQ ID NO: 6) |
| R13 | CAG ACT GAC TCG A (SEQ ID NO: 7) |
| R12 | CAG ACT GAC TCG (SEQ ID NO: 8) |
| R11 | CAG ACT GAC TC (SEQ ID NO: 9) |
| mRNA (Pre) | Bio/C AAC UGU UAA UUA AAU UAA AUU AAA AAG GAA AUA AAA AUG UUU GAA AGU AAG UAC GUA AAU CUA CUG CUG AAC UC$^d$ (SEQ ID NO: 10) |
| mRNA (Post) | Bio/C AAC UGU UAA UUA AAU UAA AUU AAA AAG GAA AUA AAA AUG UUU GAA AGU AAG UAC GUA AAU CUA CUG CUG AAC UC$^d$ (SEQ ID NO: 11) |
| R15' | A$_{25}$/CT CAA GAG CAG TAG ATT TAC G$^e$ (SEQ ID NO: 12) |

$^a$Bio: biotin labeled;
$^b$RNA nucleotides;
$^c$Functionalized with 25 units of A.
$^d$Bold indicating the ribosome-uncovered nucleotides; underscored indicating the segment for probing.
$^e$Underscored indicating the complementary nucleotides to the mRNA.

Example 1.4. Enzyme-DNA Interaction and Ribosome Translocation

FIG. 4 illustrates two examples of Enzyme-DNA interaction and ribosome translocation. The first was to determine the cleavage site of DpnII, an endonuclease. From the sequence in FIG. 4A, a 11-nt fragment with biotin label will be produced after the enzymatic cleavage. This fragment was measured by DNA rulers from R15 to R11. The transition of the presence of particles occurred at R11 (FIG. 4B). Therefore, the exact cleavage position of DpnII was confirmed by Applicants' method.

The ribosome movement on the mRNA during translocation was also measured. For the pre-translocation state (Pre), the ribosome (indicated by the two orange ovals) occupies the position on the mRNA with 15-nt exposed to bind with the magnetically labeled oligonucleotide strand. If translocation took place, the ribosome would move three nts to reach the post-translocation (Post) position. Consequently, the mRNA would have only 12-nt to hybridize with the magnetically labeled oligonucelotide strand (FIG. 4C). The 3-nt difference can be revealed by oligonucleotide ruler strand R15' modulated at 80 pN, because R15' was only able to completely replace the 12-bp duplex between Post and the magnetically labeled oligonucelotide strand, leaving no particles on the sample surface (FIG. 4D). The force value just exceeds the expected dissociation force for the 15-bp DNA/RNA duplex.

Example 1.5. Drug-Nucleotide Binding

Figure 5A:
FIG. 5A shows a DNA duplex, with one end labeled with magnetic particle and the other end labeled with biotin.
Figure 5B:
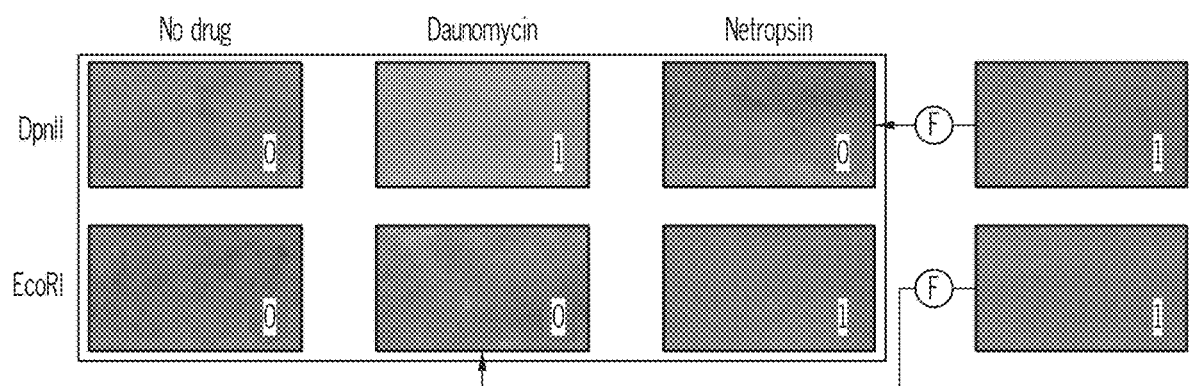
FIG. 5B shows sample images at different combinations of two drug molecules and two enzymes. The two images on the right are for the same samples indicated by the respective arrows, but prior to applying a ~1 pN force.

The derived scheme presented in FIG. 1D was used to precisely determine the binding sites of drug molecules. FIG. 5A shows the sequence of a DNA duplex, which contains two enzyme-binding segments for DpnII and EcoRI. FIG. 5B shows the results. When no drugs were in the sample, either enzyme will cleave the duplex, leading no magnetic particles being immobilized (left column). When daunomycin was present with DpnII, particle immobilization was observed, indicating that daunomycin blocked the binding site of DpnII, leaving the duplex intact, so the magnetic particles can be immobilized on the surface.

When netropsin and DpnII were present, the sample was clear with no immobilized particles. This is because netropsin does not interfere with the binding of DpnII (confirmed in FIG. 5B). However, the contrast between netropsin and daunomycin could only be revealed after applying a weak force of ~1 pN, showing the crucial role of force modulation.

The preferred binding of netropsin was confirmed when a different endonuclease, EcoRI, was used. The results (second row of FIG. 5B) show that netropsin was able to block EcoRI whereas daunomycin could not. Again, a ~1 pN force modulation was required to distinguish the different behavior between the two drugs. The results showed that using Applicants' force-modulation method and an enzyme, the specific binding site of drug molecules can be determined visually.

Figure 5C:
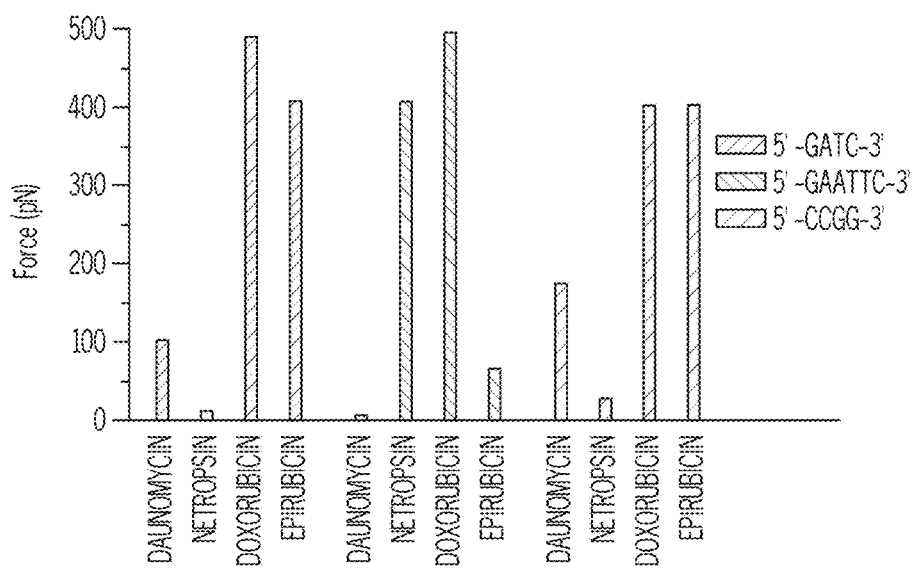
FIG. 5C plots the dissociation forces of four different drug molecules interacting with two different sequences.

The dissociation force can be further used to quantitatively distinguish the binding strength of different drug molecules at each and every specific nucleotide sequence. FIG. 5C plots the dissociation forces of four different drug molecules interacting with three different sequences. The red section shows the drugs (daunomycin, netropsin, doxorubicin, and epirubicin) binding with the segment of the DNA shown in FIG. 5A. This segment is specifically chosen because of the addition of enzyme DpnII.

The results clearly indicate the order of binding strength for this particular sequence is daunomycin, doxorubicin > epirubicin >> daunomycin >> netropsin. The blue section shows the four drugs binding with the segment, specified by the presence of EcoRI. Interestingly, netropsin becomes the second strongest. Another interesting observation is that epirubicin is more sequence-selective than doxorubicin, although the two molecules only differ by a chiral center, with the same chemical formula. This result is consistent with the fact that epirubicin appears to be less toxic in chemotherapy. This example shows the quantitative measurements of drug-DNA interaction for any given sequence by choosing the appropriate enzyme, which cannot be resolved by any existing techniques.

Example 1.6. Multiplexed Detection and Quantification with a Device

Figure 6A:
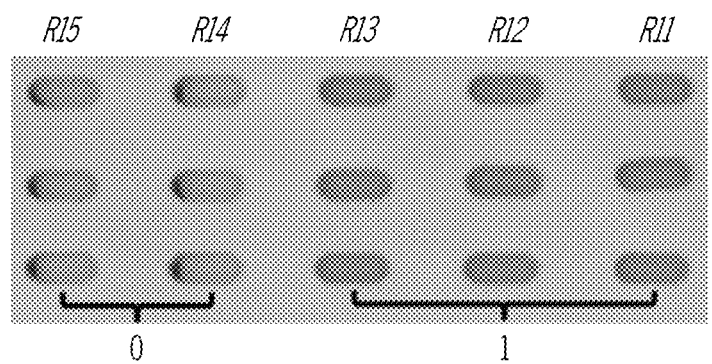
FIG. 6A shows three identical rows of experiments using R15-R11 to probe A13. Scale bar: 4 mm.

Multiplexed detection is usually required for high-throughput biosensing and analysis. In addition, quantification of immobilized particles is needed to extract key biophysical parameters. FIG. 6 shows both tasks can be achieved with the currently disclosed method. In FIG. 6A, the experiment disclosed in FIG. 2A was repeated three times, with all samples on a single plate. The results are consistent with the previous results, in that the transition of signal occurred at R13. This result showed both the feasibility of multiplexed detection and the reliability of Applicants' method.

Figure 6B:
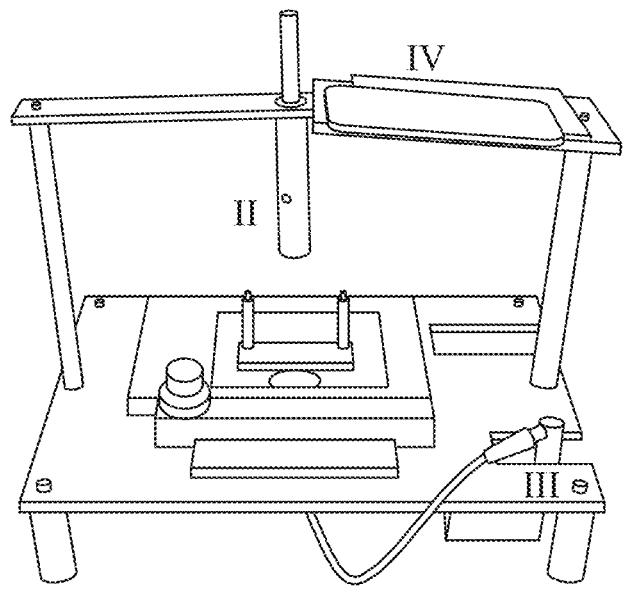
FIG. 6B shows a device to measure the transmission of the sample. I: multiplexed sample holder; II: laser pointer as light source; III: voltmeter connected to a photodiode beneath the sample; IV: holder for smartphone.
Figure 6C:
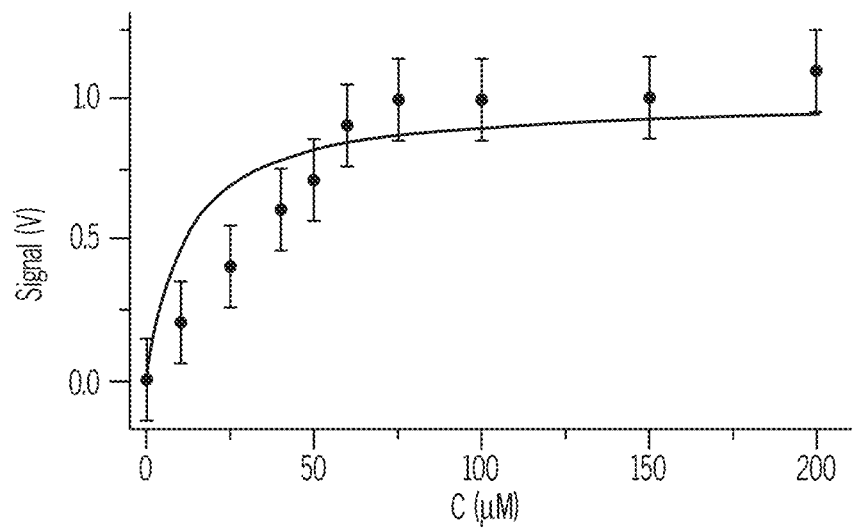
FIG. 6C shows transmission of samples containing different concentrations of drug molecules. Fitting gives a binding constant of $9\pm2\times10^4$ $M^{-1}$.

FIG. 6B shows a photo of a novel and inexpensive device that measures the transmission of a laser beam after passing through each sample. The detection was achieved by using a photodetector (DET100A, Thorlabs) coupled with a voltmeter. FIG. 6C shows the results of samples containing different concentrations of daunomycin. Fitting of the profile yielded a binding constant of $9\pm2\times10^4$ $M^{-1}$, consistent with the results using a sensitive atomic magnetometer.

Example 1.7. A Unique Design for Sample Holders

Applicants' method of force-modulated hybridization requires three unique steps. In some embodiments, the first step is to hybridize the involved DNA/RNA strands at the specific biological condition for each application. In some embodiments, the second step is to perform surface immobilization. In some embodiments, the third step is to apply a mechanical force on the sample. This sample manipulation leads to a specific design of sample holders.

A shown in FIG. 7A, a new system was designed consisting of a puncher, an incubator, and a displayer. After incubating the sample, the puncher will be used to break the bottom of the incubator so the sample will be transferred to the corresponding wells on the displayer. The bottom of the displayer was functionalized, for example with streptavidin, so that magnetic particles will be able to be immobilized through a labeled DNA duplex, for example with biotin. A mechanical force is then applied on the displayer followed by final inspection and measurement.

As shown in FIG. 7B, mechanical force can be achieved for multiplexed sample wells. The samples within each lane were under identical conditions. 1: DNA duplex with 100 μM daunorubicin and DpnII; 2: DNA duplex with 100 μM netropsin and DpnII; 3: DNA duplex; 4: DNA duplex incubated with 100 μM daunomycin and EcoRI; 5: DNA duplex with 100 μM netropsin and ECoRI. After applying ultrasound through a piezo plate, only the particles in lanes 2 and 5 were removed, indicating weak binding between netropsin and CTAG (lane 2), and between daunomycin and the EcoRI binding site (lane 4). These results are consistent with the results in FIG. 5.

Example 1.8. Sequencing Using the DNA Rulers

Figure 8:
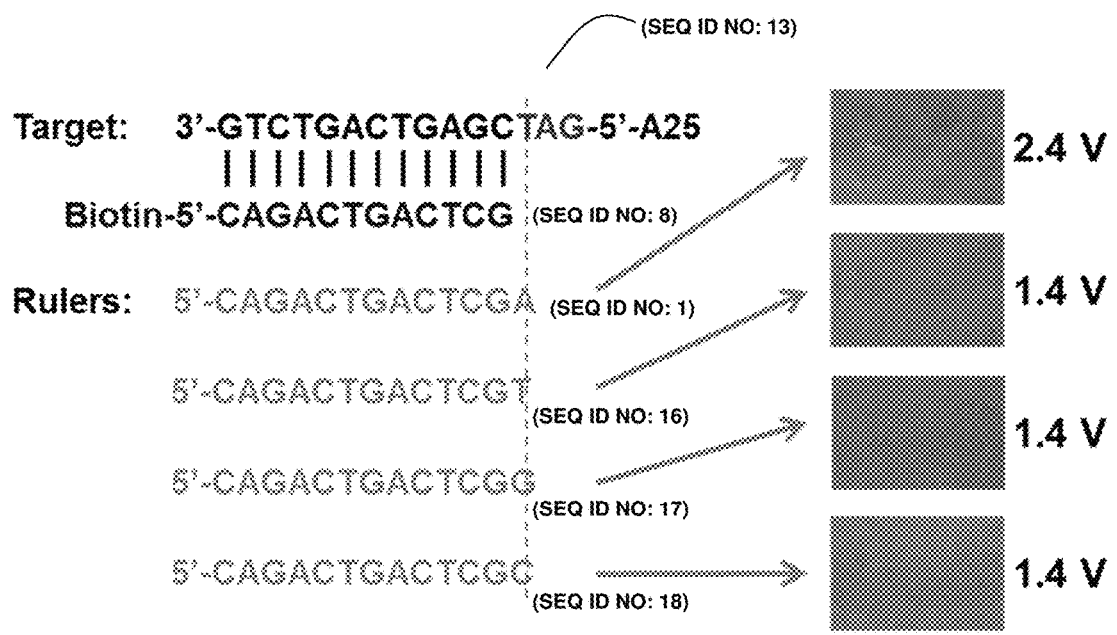
FIG. 8 depicts, in accordance with embodiments herein, the use of a series of oligonucleotide ruler strands to sequence the unknown nucleotides on a target DNA.

The precise DNA rulers can be used for sequencing, which will be particularly suited for sequencing short DNA or RNA strands. These types of strands are difficult to directly sequence because of their limited length. FIG. 8 shows the use of a series of oligonucleotide ruler strands to sequence the unknown nucleotides on a target DNA. The target has a segment of known sequence followed by unknown ones in red (T, then A and G, in this example). The four ruler DNAs, which differ by only the last nucleotide, were respectively mixed with the target and a DNA with biotin label that is complementary to the known segment of the target, at a ratio of 2:1:1. Only when the oligonucleotide ruler strand contains the complementary nucleotide with the unknown one on the target (A in this example), the sample well showed no particles.

Two detection methods were used. One was photos taken by a smart phone. A clear photo indicates no particles, whereas a yellow photo indicates the presence of particles. The other technique was the device shown in FIG. 6B, a high voltage indicates (2.2-2.4 V) no particles, and a low voltage indicates particles (1.4-1.5 V). Using the same principle, the next unknown nucleotides (A and G in this example) can be identified step by step. In each step, a set of oligonucleotide ruler strand will be used.

The various methods and techniques described above provide a number of ways to carry out the invention. It is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of determining the length of an analyte strand, comprising:
   (a) incubating a magnetically labeled oligonucleotide strand, the analyte strand, and one of a series of oligonucleotide ruler strands to form a mixture,
      wherein the magnetically labeled oligonucleotide strand is complementary in sequence to the analyte strand,
      wherein the series of oligonucleotide ruler strands are complementary in sequence to the magnetically labeled oligonucleotide strand and comprise different lengths, and
      wherein either the analyte strand or the oligonucleotide ruler strands are labeled with at least one label;
   (b) transferring the mixture to a surface functionalized to couple with the at least one label;
   (c) applying a mechanical force to the mixture; and
   (d) inspecting the surface for immobilized particles,
      wherein if the analyte strand is labeled, then the longest oligonucleotide ruler strand producing immobilized particles on the surface represents the length of the analyte strand, and
      wherein if the oligonucleotide ruler strands are labeled, then the longest oligonucleotide ruler strand not producing immobilized particles represents the length of the analyte strand; and
   (e) wherein a different oligonucleotide ruler strand is used to repeat steps (a)-(d) until the length of the analyte strand is determined.

2. The method of claim 1,
   wherein the mechanical force modulates oligonucleotide hybridization;
   wherein the oligonucleotide hybridization results in the presence of immobilized particles when the analyte strand is labeled and the oligonucleotide ruler strand is not longer than the analyte strand, and wherein the immobilized particles represent a hybrid structure between the magnetically labeled oligonucleotide strand and the analyte strand;

wherein the oligonucleotide hybridization results in the absence of immobilized particles when the analyte strand is labeled and the oligonucleotide ruler strand is longer than the analyte strand;

wherein the oligonucleotide hybridization results in the presence of immobilized particles when the oligonucleotide ruler strands are labeled and the oligonucleotide ruler strand is longer than the analyte strand, and wherein the immobilized particles represent a hybrid structure between the magnetically labeled oligonucleotide strand and the oligonucleotide ruler strand; and wherein the oligonucleotide hybridization results in the absence of immobilized particles when the oligonucleotide ruler strands are labeled and the oligonucleotide ruler strand is shorter than or the same length as the analyte strand.

3. The method of claim 1, wherein the analyte strand is labeled with the at least one label.

4. The method of claim 1, wherein the oligonucleotide ruler strands are labeled with the at least one label.

5. The method of claim 1, wherein the immobilized particles are represented by a yellow color on the surface, and wherein the yellow color is derived from the magnetically labeled oligonucleotide strand.

6. The method of claim 1,
wherein the analyte strand is a DNA strand or an RNA strand;
wherein the magnetically labeled oligonucleotide strand is a DNA strand or an RNA strand;
wherein the magnetically labeled oligonucleotide strand has a longer length than the analyte strand;
wherein the magnetically labeled oligonucleotide strand is 12-50 nucleotides long; and
wherein the magnetically labeled oligonucleotide strand is labeled with a magnetic particle.

7. The method of claim 1,
wherein the oligonucleotide ruler strands are selected from the group consisting of DNA strands, RNA strands, and combinations thereof;
wherein the oligonucleotide ruler strands are complementary in sequence to the analyte strand; and
wherein the oligonucleotide ruler strands comprise oligonucleotides longer than the analyte strand, oligonucleotides shorter than the analyte strand, and oligonucleotides the same length as the analyte strand.

8. The method of claim 1,
wherein the surface is functionalized with a molecule that binds to the at least one label; and
wherein the at least one label is selected from the group consisting of biotin, streptavidin, digoxigenin, avidin, maleic imide, gold, proteins, nucleic acids, functional groups, and combinations thereof.

9. The method of claim 1,
wherein the mechanical force is selected from the group consisting of gravitational force, centrifugal force, shaking force, ultrasound radiation force, magnetic force, and combinations thereof; and
wherein the mechanical force applied is between 10 fN and 500 pN.

10. The method of claim 1, wherein the at least one label is biotin, and wherein the surface is functionalized with streptavidin.

11. The method of claim 1, wherein the inspecting occurs by visual inspection.

* * * * *